# United States Patent
Sasaki et al.

(10) Patent No.: US 7,829,307 B2
(45) Date of Patent: Nov. 9, 2010

(54) PRODUCTION OF GLUCAGON-LIKE PEPTIDE 2

(75) Inventors: Ken Sasaki, Thornhill (CA); Vanessa Jane Williamson, Guelph (CA); Alberto de Araujo, Mississauga (CA); Ewa Walczyk, Caledon (CA)

(73) Assignee: NPS Pharmaceuticals, Inc., Bedminster, NJ (US)

( * ) Notice: Subject to any disclaimer, the term of this patent is extended or adjusted under 35 U.S.C. 154(b) by 0 days.

(21) Appl. No.: 10/993,127

(22) Filed: Nov. 22, 2004

(65) Prior Publication Data

US 2005/0164930 A1 Jul. 28, 2005

Related U.S. Application Data

(60) Provisional application No. 60/523,667, filed on Nov. 21, 2003.

(51) Int. Cl.
*A61K 38/28* (2006.01)
*A61K 38/48* (2006.01)
*C12P 21/06* (2006.01)

(52) U.S. Cl. .................. 435/69.1; 424/94.64; 435/68.1; 530/308

(58) Field of Classification Search ........................ None
See application file for complete search history.

(56) References Cited

U.S. PATENT DOCUMENTS

| | | | |
|---|---|---|---|
| 4,336,336 A | 6/1982 | Silhavy et al. | |
| 4,551,433 A | 11/1985 | DeBoer | |
| 4,588,684 A | 5/1986 | Brake | |
| 4,689,406 A | 8/1987 | Banks et al. | |
| 4,738,921 A | 4/1988 | Belagaje et al. | |
| 4,745,056 A | 5/1988 | Guterman et al. | |
| 4,837,148 A | 6/1989 | Cregg | |
| 4,870,023 A | 9/1989 | Fraser et al. | |
| 4,873,192 A | 10/1989 | Kunkel | |
| 4,876,197 A | 10/1989 | Burke et al. | |
| 4,880,734 A | 11/1989 | Burke et al. | |
| 4,929,555 A | 5/1990 | Cregg et al. | |
| 5,110,729 A | 5/1992 | Maeda et al. | |
| 5,352,771 A | 10/1994 | Kostic et al. | |
| 5,393,924 A | 2/1995 | Tafesh et al. | |
| 5,416,007 A | 5/1995 | Charette et al. | |
| 5,420,242 A | 5/1995 | Gautvik et al. | |
| 5,457,066 A | 10/1995 | Frank et al. | |
| 5,580,751 A | 12/1996 | Buchardt et al. | |
| 5,595,887 A | 1/1997 | Coolidge et al. | |
| 5,602,034 A | 2/1997 | Tekamp-Olson | |
| 5,629,205 A | 5/1997 | Lagosky | |
| 5,707,826 A | 1/1998 | Wagner et al. | |
| 5,728,543 A | 3/1998 | Dorschug et al. | |
| 5,789,379 A | 8/1998 | Drucker et al. | |
| 5,814,603 A | 9/1998 | Oldenburg et al. | |
| 5,851,810 A | 12/1998 | Blanchard | |
| 5,853,976 A | 12/1998 | Hesse et al. | |
| 5,912,229 A * | 6/1999 | Thim et al. ................... 514/12 |
| 6,130,063 A | 10/2000 | Lawlis | |
| 6,171,823 B1 | 1/2001 | Woldike et al. | |
| 6,184,201 B1 | 2/2001 | Drucker et al. | |
| 6,313,092 B1 | 11/2001 | Holladay et al. | |
| 6,316,224 B1 | 11/2001 | Xia | |
| 6,461,834 B1 | 10/2002 | Dormady et al. | |
| 6,660,758 B1 | 12/2003 | Nicolaou et al. | |
| 6,660,763 B2 | 12/2003 | Tang et al. | |
| 6,703,484 B2 | 3/2004 | Chatterjee et al. | |
| 7,335,486 B2 | 2/2008 | Wagner et al. | |
| 2005/0221444 A1 | 10/2005 | Williams et al. | |
| 2005/0227313 A1 | 10/2005 | Seo et al. | |
| 2005/0260701 A1 | 11/2005 | Wagner et al. | |
| 2005/0287632 A1 | 12/2005 | Holmquist et al. | |
| 2006/0008870 A1 | 1/2006 | Wagner et al. | |
| 2006/0024778 A1 * | 2/2006 | Wagner et al. ............. 435/68.1 |

FOREIGN PATENT DOCUMENTS

| | | |
|---|---|---|
| EP | 0164556 A2 | 12/1958 |
| EP | 0036259 A2 | 9/1981 |
| EP | 0036776 A2 | 9/1981 |
| EP | 0060057 A1 | 9/1982 |
| EP | 0063953 A2 | 11/1982 |
| EP | 0121775 A1 | 10/1984 |
| EP | 0127839 A2 | 12/1984 |
| EP | 0136829 A2 | 4/1985 |
| EP | 0136907 A2 | 4/1985 |

(Continued)

OTHER PUBLICATIONS

Chang, J. (1985) *Eur. J. Biochem.* 151, 217-224.

(Continued)

*Primary Examiner*—Robert Landsman
*Assistant Examiner*—Ian Dang
(74) *Attorney, Agent, or Firm*—Stoel Rives LLP

(57) ABSTRACT

GLP-2 peptides and analogs thereof are produced in high yield and with desired, authentic termini by isolation from a GLP-2 peptide multimer in which at least two units of GLP-2 peptide are coupled through a linker that presents an N-terminal acid cleavage site and a C-terminal enzyme cleavage site. In a specific embodiment, [Gly$^2$]hGLP-2 is produced from a multimeric precursor comprising 2-30 units thereof.

4 Claims, 12 Drawing Sheets

FOREIGN PATENT DOCUMENTS

| | | |
|---|---|---|
| EP | 0155476 A1 | 9/1985 |
| EP | 0267851 A2 | 5/1988 |
| EP | 0284044 A1 | 9/1988 |
| EP | 0329203 A1 | 8/1989 |
| EP | 0473128 A | 3/1992 |
| EP | 0978565 A1 | 2/2000 |
| WO | WO 9317110 A2 | 9/1993 |
| WO | WO 95/17510 * | 6/1995 |
| WO | WO 9517510 A1 | 6/1995 |
| WO | WO 9617941 A2 | 6/1996 |
| WO | WO 9803664 A1 | 1/1998 |
| WO | WO 9964611 A | 12/1999 |
| WO | WO 0006763 A1 | 2/2000 |
| WO | WO 0026418 A1 | 5/2000 |
| WO | WO 0028067 A1 | 5/2000 |
| WO | WO 01/49314 A2 | 7/2001 |
| WO | WO 02061105 A2 | 8/2002 |
| WO | WO 03099848 A2 | 12/2003 |
| WO | WO 03099854 A2 | 12/2003 |
| WO | WO 03100022 A2 | 12/2003 |
| WO | WO 2004011599 A2 | 2/2004 |

OTHER PUBLICATIONS

Buhl et al., *J. Biol. Chem.*, 1988, 263(18):8621.

Advisory Action issued in U.S. Appl. No. 10/997,697 dated Oct. 1, 2008.

Advisory Action issued in U.S. Appl. No. 10/997,762 dated Jul. 15, 2008.

Aubin, et al. "Highly effective delivery of foreign DNA to adherent cells via polybrene/DMSO-assisted gene transfer", Methods Mol. Biol., 62 (1997), 319-42.

Beach, et al. "Functionally homologous cell cycle control genes in budding and fission yeast", Nature, 300(5894), Dec. 23, 1982, 706-9.

Birnstiel, et al., "Transcription termination and 3' procession: the end is in site!", Cell, 41(2), Jun. 1985, 349-59.

Catsimpoolas, et al., "Specific cleavage of cystine peptides by cyanide", J. of Biol. Chem., 241(8), Apr. 25, 1996, 1790-6.

Coombs, et al. "Substrate specificity of prostate-specific antigen (PSA)", Chem Biol. 5(9), Sep. 1998, 475-88.

Dargatz, et al., "The heterodimeric protease clostripain from *Clostridium histolyticum* is encoded by a single gene", Molecular and General Genetics, vol. 240, No. 1, Jul. 1, 1993, 140-145.

Davies, et al., "Plasmid-determined resistance to antimicrobial agents", Anu. Rev. Microbiol. 32, 1978, 469-508.

Database EMBL (online), Jul. 12, 2001, "Glucagon [*homo sapiens*]", XP002501257 retrieved from NCBI on Apr. 21, 2009, database accession No. AAH05278, the whole document.

Dijkema, et al., "Cloning and expression of the chromosomal immune interferon gene of the rat", EMBO J. 4(3), Mar. 1985, 761-7.

Djuran, et al., "Hydrolysis of amide bond in histidine-containing peptides promoted by chelated amino acid palladium(II) complexes: dependence of hydrolytic pathway on the coordination modes of the peptides", Polyhedron 18(27), Sep. 14, 1999, 3611-3616.

Dou, et al., "Preliminary study on the cleavage of fusion protein GST-CMIV with palladate(II) complex", Preparative Biochem. & Biotechnol. 2000, vol. 30, No. 1, 69-78.

Drexler, et al., "Palladium(II) and platinum(II) complexes with 1,5-dithiacycolooctane(dtco): structures of Pd(dtco)Cl$_2$ and Pd(dtco$_2$)(NO$_3$)$_2$ and kinetics of ligand substitution in [Pd(dtco$_2$)]$^{2+}$ by bidenate ligands", Inorganic Chemistry, 30, 1991, 1297-1302.

Dykes, et al., "Expression of atrial natriuretic factor as a cleavable fusion protein with chloramphenicol acetyltransferase in *Escherichia coli*", Eur. J. Biochem., 174(2), Jun. 1, 1988, 411-6.

Felgner, et al., "Enhanced gene delivery and mechanism studies with a novel series of cationic lipid formulations", J. Biol. Chem. 269(4), Jan. 28, 1994, 2550-61.

Forsberg, et al., "An evaluation of different enzymatic cleavage methods for recombinant fusion proteins, applied on des(1-3)insulin-like growth factor I", J. Protein Chem., 11(2), Apr. 1992, 201-11.

Forsberg, et al., "Comparison of two chemical cleavage methods for preparation of a truncated form of recombinant human insulin-like growth factor I from a secreted fusion protein", Biofactors, 2(2), Dec. 1989, 105-12.

Gluzman, "SV40-Transformed simian cells support the replication of early sv40 mutants", Cell, 23(1), Jan. 1981, 175-182.

Gram, et al., "A novel approach for high level production of a recombinant human parathyroid hormone fragment in *Escherichia coli*", Bio/Technology, 12(10), Oct. 1994, 1017-23.

Greger, et al., "Poly(A) signals control both transcriptional termination and initiation between the tandem GAL10 and GAL7 genes of *Saccharomyces cerevisiae*", EMBO J. 17(16), Aug. 17, 1998, 4771-9.

Guo, et al., "Protein tolerance to random amino acid change", 2004, Proc. Natl. Acad. Sci. 101: 9205-9210.

Hill, "Functional analysis of conserved histidines in ADP-Glucose pyrophophorylase from *Escherichia coli*", 1998, Biochem. Biophys. Res. Comm. 244:573-577.

Hohmann, et al., "Rate and equilibrium data for substitution reactions of diaqua(ethylenediamine)palladium(II) with chloride in aqueous solution", Inorg Chim Acta, 174(1), 1990, 87-92.

International Preliminary Examination Report issued in International Application No. PCT/US2003/16645 mailed Nov. 12, 2004.

International Search Report issued in International Application No. PCT/US2003/16645 mailed May 24, 2004.

International Preliminary Examination Report issued in International Application No. PCT/US2003/16469 mailed Feb. 9, 2005.

International Search Report issued in International Application No. PCT/US2003/16469 mailed Oct. 28, 2004.

International Preliminary Examination Report issued in International Application No. PCT/US2003/16470 mailed Jul. 6, 2005.

International Search Report issued in International Application No. PCT/US2003/16470 mailed Jul. 21, 2004.

International Preliminary Examination Report issued in International Application No. PCT/US2003/16649 dated May 15, 2007.

International Search Report issued in International Application No. PCT/US2003/16649 dated Dec. 11, 2006.

International Search Report issued in International Application No. PCT/US2003/16647 dated Jul. 2, 2004.

International Preliminary Examination Report issued in International Application No. PCT/US2003/16647 dated Aug. 23, 2004.

International Search Report issued in International Application No. PCT/US2003/16642 dated Sep. 3, 2004.

International Preliminary Examination Report issued in International Application No. PCT/US2003/16642 dated Mar. 6, 2006.

International Search Report issued in International Application No. PCT/US2003/16643 dated Jul. 20, 2004.

International Preliminary Examination Report issued in International Application No. PCT/US2003/16643 dated Aug. 21, 2004.

International Preliminary Examination Report issued in International Application No. PCT/US2003/16468 dated Dec. 16, 2004.

International Search Report issued in International Application No. PCT/US2003/16468 dated Jan. 15, 2004.

International Preliminary Examination Report issued in International Application No. PCT/IB2004/004439 dated May 22, 2006.

International Search Report issued in International Application No. PCT/IB2004/004439 dated Sep. 23, 2005.

Ito, et al., "Transformation of intact yeast cells treated with alkali cations", J. Bacteriol, 153(1), Jan. 1983, 163-8.

Kaufman et al., "The phosphorylation state of eucaryotic initiation factor 2 alters translational efficiency of specific mRNAs", Mol. Cell Biol., 9(3), Mar. 1989, 946-58.

Knott, et al., "The isolation and characterization of human atrial natriuretic factor produced as a fusion protein in *Escherichia coli*", Eur. J. Biochem., 174(2), Jun. 1, 1988, 405-10.

Kohrer, et al., "Import of amber and ochre suppressor tRNAs into mammalian cells: a general approach to site-specific insertion of amino acid analogues into proteins", Proc. Natl. Acad. Sci. USA, 98(25), Dec. 4, 2001, 14310-5.

Kowal, et al., "Twenty-first aminoacyl-tRNA synthetase-suppressor tRNA pairs for possible use in site-specific incorporation of amino acid analogues into proteins in eukaryotes and in eubacteria", Proc. Natl. Acad. Sci. USA 98(5), Feb. 27, 2001, 2268-73.

Kunkel, T.A., "Rapid and efficient site-specific mutagenesis without phenotypic selection", Proc. Natl. Acad. Sci. USA, 82, 1985 488-492.

Kurtz, et al., "Integrative transformation of *Candida albicans*, using a cloned Candida ADE2 gene", Mol. Cell Biol., 6(1), Jan. 1986, 142-9.

Labouesse, B., "La Clostripaine, Protease De Clostridium Histolyticum II.—Specificite", Bull. Soc. Chim. Biol., 42, 1960, 559-568.

Lazar, et al., "Transforming growth factor α: mutation of aspartic acid 47 and leucine 48 results in different biological activities", 1988, Mol. Cell Biol. 8:1247-1252.

Lebacq-Verheyden, et al., "Posttranslational processing of endogenous and of baculovirus-expressed human gastrin-releasing peptide precursor", Mol. Cell Biol. 8(8), Aug. 1988 3129-35.

Lee et al., "Enhanced expression of tandem multimers of the antimicrobial peptide buforin II in *Escherichia coli* by the DEAD-box protein and trxB mutant", Appl. Microbiol. Biotechnol. 58(6), May 2002, 790-6.

Lidell, et al., "An autocatalytic cleavage in the C terminus of the human MUC2 mucin occurs at the low pH of the late secretory pathway", J. Biol. Chem., vol. 278, No. 16, Apr. 18, 2003, 13944-13951.

Maniatis, et al., "Regulation of inducible and tissue-specific gene expression", Science, 236(4806), Jun. 5, 1987, 1237-45.

Marcus, F., "Preferential cleavage at aspartyl-prolyl peptide bonds in dilute acid", Int. J. Pept. Protein Res., 25(5), May 1985, 542-6.

Marczinovits et al., "An alternative purification protocol for producing hepatitis B virus X antigen on a preparative scale in *Escherichia coli*", J. Biotechnology, 1997, vol. 56, 81-88.

Marumoto, et al., "Hyperproduction of polyhedrin-IGF II infusion protein in silkworm larvae infected with recombinant *Bombyx mori* nuclear polyhedrosis virus", J. Gen. Virol., 68 (pt10), 1987, 2599-2606.

Masson, et al., "Transformation of *Bacillus thuringiensis* vegetative cells by electroporation", FEMS Microbiol. Lett., 60(3), Aug. 1989, 273-7.

McCarroll, et al., "Stable insect cell cultures for recombinant protein production", Curr Opin Biotechnol. 8(5), Oct. 1997, 590-4.

Meiwes, et al., "Clostripain: production and use for peptide synthesis", Biomedica Biochimica Acta, 1991, vol. 50, No. 10-11, S80-S83.

Milovic, et al. "Interplay of terminal amino group and coordinating side chains in directing regioselective cleavage of natural peptides and proteins with palladium(II) complexes", Inorganic Chemistry, Dec. 2002, vol. 41, No. 26.

Milovic, et al., "Palladium(II) and platinum(II) complexes as synthetic peptidases", Metal Ions Biol. Syst., 38, 2001, 145-186.

Milovic, et al., "Palladium(II) complexes, as synthetic peptidases, regioselectively cleave the second peptide bond 'upstream' from methionine and histidine side chains", J. Amer. Chem. Soc. 124(17), 2002, 4759-4769.

Mitchell, et al., "Purification and properties of Clostridiopeptidase B (Clostripain)", J. Biol. Chem., vol. 243, No. 18, 1968, 4683-4692.

Mitchell, "Cleavage at arginine residues by clostripain", Methods in Enzymology, Academic Press Inc., vol. 47, Jan. 1977, 165-170.

Miyanohara, et al., "Expression of hepatitis B surface antigen gene in yeast", Proc. Natl. Acad. Sci. USA, 801(1), Jan. 1983, 1-5.

Moks, et al., "Expression of human insulin-like growth factor I in bacteria: use of optimized gene fusion vectors to facilitate protein purification", Biochemistry, 26(17), Aug. 25, 1987, 5239-44.

Nilsson, et al., "Multiple affinity domains for the detection, purification and immobilization of recombinant proteins", J. of Molecular Recognition, 9(5/6), 1996, John Wiley & Sons, Dec. 9, 1996, 585-594.

Notice of Allowance issued in U.S. Appl. No. 10/997,822 dated May 14, 2009.

Notice of Allowance issued in U.S. Appl. No. 10/997,078 dated Oct. 23, 2008.

Notice of Allowance issued in U.S. Appl. No. 11/944,165 dated Oct. 15, 2008.

Notice of Allowance issued in U.S. Appl. No. 10/997,074 dated Sep. 21, 2007.

Office Action (non-final) issued in U.S. Appl. No. 10/997,074 dated Dec. 15, 2006.

Office Action (non-final) issued in U.S. Appl. No. 10/997,065 dated Jan. 18, 2008.

Office Action (non-final) issued in U.S. Appl. No. 10/997,065 dated Oct. 21, 2008.

Office Action (non-final) issued in U.S. Appl. No. 10/997,078 dated Jul. 25, 2007.

Office Action (non-final) issued in U.S. Appl. No. 10/997,700 dated Oct. 4, 2007.

Office Action (non-final) issued in U.S. Appl. No. 10/997,700 dated Apr. 7, 2008.

Office Action (non-final) issued in U.S. Appl. No. 10/997,697 dated Sep. 11, 2007.

Office Action (final) issued in U.S. Appl. No. 10/997,697 dated Jul. 7, 2008.

Office Action (non-final) issued in U.S. Appl. No. 10/997,697 dated Mar. 2, 2009.

Office Action (non-final) issued in U.S. Appl. No. 10/997,078 dated Jan. 9, 2008.

Office Action (final) issued in U.S. Appl. No. 10/997,078 dated Jul. 23, 2008.

Office Action (non-final) issued in U.S. Appl. No. 10/997,822 dated Oct. 4, 2007.

Office Action (non-final) issued in U.S. Appl. No. 10/997,822 dated Apr. 30, 2008.

Office Action (non-final) issued in U.S. Appl. No. 10/997,822 dated Nov. 14, 2008.

Office Action (non-final) issued in U.S. Appl. No. 10/997,762 dated Oct. 9, 2007.

Office Action (non-final) issued in U.S. Appl. No. 11/944,165 dated May 30, 2008.

Office Action (final) issued in U.S. Appl. No. 10/997,762 dated Apr. 17, 2008.

Office Action (non-final) issued in U.S. Appl. No. 11/997,762 dated Jan. 7, 2009.

Office Action (non-final) issued in U.S. Appl. No. 11/997,762 dated Apr. 2, 2009.

Okamoto, et al., "Structural characterization of argingipain, a novel arginine-specific cysteine proteinase as a major periodontal pathogenic factor from *Porphyromonas gingivalis*", Archives of Biochemistry and Biophysics, 316(2), Feb. 1, 1995, 917-925.

Orskov, et al., "Biological effects and metabolic rates of glucagonlike peptide-1 7-36 amide and glucagonlike peptide-1 7-37 in healthy subjects are indistinguishable", Diabetes, 42(5), May 1993, 658-661.

Parac, et al., "New regioselectivity in the cleavage of histidine-containing peptides by palladium(II) complexes studied by kinetic experiments and molecular dynamics simulations", J. Am. Chem. Soc., 1999, 121:3127-3135.

Park, Sang-Ho, et al., "Role of proline, cysteine and a disulphide bridge in the structure and activity of the anti-microbial peptide gaegurin 5", Biochem. J. 368(Pt 1), 2002, 171-182.

Pearson, "Searching protein sequence libraries: comparison of the sensitivity and selectivity of the Smith-Waterman and FASTA alogorithms", Genomics, 11(3), Nov. 1991, 635-50.

Piers, et al., "Recombinant DNA procedures for producing small antimicrobial cationic peptides in bacteria", Gene, 134(1), Nov. 30, 1993, 7-13.

Pilon, et al., "Ubiquitin fusion technology: bioprocessing of peptides", Biotechnol. Prog., 13(4), Jul.-Aug. 1997, 374-9.

Pop, et al., "The twin-arginine signal peptide of phoD and the TatA$_d$/C$_d$ proteins *Bacillus subtillis* from an autonomous tat translocation system", J. Biological Chem., 277(5), American Society of Biochemical Biologists, Birmingham, Feb. 1, 2002, 3268-3273.

Raibaud, et al., "Positive control of transcription initiation in bacteria", Annu. Rev. Genet., 18, 1984, 173-206.

Rau, et al., "Complex formation and ligand substitution reactions of (2-picolylamine)palladium(II) with various biologically relevant ligands. Characterization of (2-picolylamine)(1,1-cyclobutanedicarboxylato)palladium(II)", Inorganic Chemistry, 36, 1997, 1454-1463.

Ray, et al., "Production of recombinant salmon calcitonin by in vitro amidation of an *Escherichia coli* produced precursor peptide", Bio/Technology 11(1), Jan. 1993, 64-70.

Response to Office Action filed in U.S. Appl. No. 10/997,697, filed Mar. 5, 2008.

Response after final Office Action filed in U.S. Appl. No. 10/997,697, filed Sep. 8, 2008.

Request for Continued Examination filed in U.S. Appl. No. 10/997,697, filed Nov. 7, 2008.
Response to Restriction Requirement filed in U.S. Appl. No. 10/997,697, filed Apr. 5, 2007.
Restriction Requirement issued in U.S. Appl. No. 10/997,697 dated Feb. 21, 2007.
Response to Office Action filed in U.S. Appl. No. 10/997,078, filed Oct. 25, 2007.
Response to Office Action filed in U.S. Appl. No. 10/997,078, filed Apr. 8, 2008.
Response after final Office Action filed in U.S. Appl. No. 10/997,078, filed Sep. 23, 2008.
Response to Restriction Requirement filed in U.S. Appl. No. 10/997,078, filed May 2, 2007.
Restriction Requirement issued in U.S. Appl. No. 10/997,078 dated Apr. 2, 2007.
Response to Office Action filed in U.S. Appl. No. 10/997,822, filed Jan. 3, 2008.
Response to Office Action filed in U.S. Appl. No. 10/997,822, filed Jul. 30, 2008.
Response to Office Action filed in U.S. Appl. No. 10/997,822, filed Feb. 17, 2009.
Response to Restriction Requirement filed in U.S. Appl. No. 10/997,822, filed Jul. 25, 2007.
Restriction Requirement issued in U.S. Appl. No. 10/997,822 dated Jun. 25, 2007.
Response to Office Action filed in U.S. Appl. No. 11/944,165, filed Aug. 29, 2008.
Response to Office Action filed in U.S. Appl. No. 10/997,074, filed Feb. 22, 2007.
Response to Restriction Requirement filed in U.S. Appl. No. 10/997,074, filed Nov. 27, 2006.
Restriction Requirement issued in U.S. Appl. No. 10/997,074 dated Oct. 26, 2006.
Response to Office Action filed in U.S. Appl. No. 10/997,762, filed Jan. 9, 2008.
Response after final Office Action filed in U.S. Appl. No. 10/997,762, filed Jun. 17, 2008.
Response to Office Action filed in U.S. Appl. No. 10/997,762, filed Jan. 21, 2009.
Request for Continued Examination filed in U.S. Appl. No. 10/997,762, filed Oct. 17, 2008.
Response to Restriction Requirement filed in U.S. Appl. No. 10/997,762, filed Jul. 17, 2007.
Restriction Requirement issued in U.S. Appl. No. 10/997,762 dated Jun. 18, 2007.
Restriction Requirement issued in U.S. Appl. No. 10/997,065, dated Apr. 10, 2007.
Response to Restriction Requirement filed in U.S. Appl. No. 10/997,065, filed Aug. 8, 2007.
Response to Office Action filed in U.S. Appl. No. 10/997,065, filed Jul. 18, 2008.
Response to Office Action filed in U.S. Appl. No. 10/997,065, filed Apr. 21, 2009.
Response to Office Action filed in U.S. Appl. No. 10/997,700, filed Jan. 4, 2008.
Response to Office Action filed in U.S. Appl. No. 10/997,700, filed Jan. 12, 2009.
Restriction Requirement issued in U.S. Appl. No. 10/997,700 dated Jul. 3, 2007.
Response to Restriction Requirement filed in U.S. Appl. No. 10/997,700, filed Jul. 30, 2007.
Schellenberger, et al., "Peptide production by a combination of gene expression, chemical synthesis, and protease-catalyzed conversion", Int. J. Pept. Protein Res., 41(4), Apr. 1993, 326-32.
Shen, S.H., "Multiple joined genes prevent product degratation in *Escherichia coli*", Proc. Natl. Acad. Sci. USA, 81(15), Aug. 1984, 4627-31.
Shimatake, et al., "Purified λ regulatory protein cII positively activates promoters for lysogenic development", Nature, 292(5819), Jul. 9, 1981, 128-32.

Shimizu, et al., "Transfer of cloned human class I major histocompatibility complex genes into HLA mutant human lymphoblastoid cells", Mol. Cell Biol. 6(4), Apr. 1986, 1074-87.
Shine, et al., "Determinant of cistron specificity in bacterial ribosomes", Nature 254(5495), Mar. 6, 1975, 34-8.
Simmonds, et al., "Molecular interactions between Vestigial and Scalloped promote wing formation in *Drosophila*", Genes Dev. 12(24), Dec. 15, 1998, 3815-20.
Smith, et al. "Surface point mutations that significantly alter the structure and stability of a protein's denatured state", Protein Science, 1996, vol. 5, 2009-2019.
Sprengart, et al., "The downstream box: an efficient and independent translation initiation signal in *Escherichia coli*", EMBO J., 15(3), Feb. 1, 1996, 665-74.
Supplementary European Search Report issued in EP Application No. 03755506 dated Nov. 7, 2008.
Supplementary European Search Report issued in EP Application No. 03734200 dated Feb. 27, 2006.
Supplementary European Search Report issued in EP Application No. 03755504 dated Mar. 14, 2006.
Supplementary European Search Report issued in EP Application No. 03734201 dated Jul. 4, 2006.
Supplementary European Search Report issued in EP Application No. 03771535 dated Oct. 1, 2008.
Supplementary European Search Report issued in EP Application No. 03734173 dated Nov. 12, 2008.
Supplementary European Search Report issued in EP Application No. 03734172 dated Apr. 17, 2007.
Supplementary European Search Report issued in EP Application No. 03736710 dated Jun. 26, 2007.
Supplementary Partial European Search Report issued in EP Application No. 04821092.6 dated Jun. 28, 2007.
Supplementary European Search Report issued in EP Application No. 04821092.6 dated Jun. 28, 2007.
Taketo, "DNA transfection of *Escherichia coli* by electroporation" Biochim. Biophys. Acta. 949(3), Mar. 31, 1988, 318-24.
"Tertiary Structure", Tertiary Structure Biological Pages, hhttp://users.rcn.com/jkimball.ma.ultranet/biologicalpages/t/tertiarystructure.html (downloaded Aug. 31, 2009) 3 pgs.
Hooft Van Iddekinge, et al., "Nucleotide sequence of the polyhedrin gene of *Autographa californica* nuclear polyhedrosis virus", Virology, 131, 1983, 561-564.
Wang, et al., "Natural transformation in *campylobacter* species", J. Bacteriol, 171(2), Feb. 1990, 949-55.
Waterman, et al., "Pattern recognition in several sequences: consensus and alignment", Bull Math Biol., 46(4), 1984, 515-27.
Williams, et al., "Control of *drosophila* wing and haltere development by the nuclear vestigial gene product", Genes Dev., 5(12b), Dec. 1991, 2481-2495.
Witte, et al., "Clostripain linker deletion variants yield active enzyme in *Escherichia coli*: a possible function of the linker peptide as intramolecular inhibitor of clostripain automaturation", Current Microbiology, vol. 22, No. 5, Nov. 1996, 281-286.
Witte, et al. "Heterologous expression of the Clostripain gene from slostridium histolyticum in *Escherichia coli* and *bacillus subtillis*: maturation of the clostripain precursor is coupled with self-activation", Microbiology, 140, 1994, 1175-1182.
Written Opinion issued in International Application No. PCT/IB2004/004439 mailed Sep. 23, 2005.
Zhan, et al., "Structural analysis of regulatory protein domains using GST-fusion proteins", Gene, 281(1-2), Dec. 27, 2001, 1-9.
Zhao, et al., "Formation of mRNA 3' ends in eukaryotes: mechanism, regulation, and interrelationships with other steps in mRNA synthesis", Microbiol. Mol. Biol. Rev., 63(2), Jun. 1999, 405-45.
Zhu, et al. "Site-specific hydrolytic cleavage of cytochrome c and of its heme undecapeptide, promoted by coordination complexes of palladium(II)", J. Am. Chem. Soc., 116, 1994, 5218-5224.
Copending U.S. Appl. No. 10/997,065, filed May 24, 2002, for Method for Enzymatic Production of GLP-2(1-33) Peptides.
Labouesse, B., "L'Hydrolyse Du Glucagon Par La Clostripaine (*)",Bull. Soc. Chim. Biol., 42, 1960, 1293-304.

* cited by examiner

Primer KS1-5

```
              NdeI                    ┌─────────────┐
              ~~~~~~                  │ Thrombin Site│
                      BsaI            └──────┬──────┘
                      ~~~~~~                 ↓
              MetValSerGly  ProArgHis  GlyAspGly
    1  GGAATTCCAT ATGGTCTCAG GTCCGCGTCA TGGTGACGGT SerPhe
   41  TCTTTC
```

Primer KS2-3

```
         BamHI                        BsaI
         ~~~~~~                       ~~~~~~
    1  CGCGGATCCT CATTAGCGCG GACCAGAGAC CGGGTCGGTG
                            ArgPro GlySerVal ProAspThrIle·
   41  ATTTTGGTCT G                              ↑
       ..LysThrGln                        ┌──────────────┐
                                          │ Acid Cleavage Site│
                                          └──────────────┘
```

Figure 1

```
                    NdeI
                  ~~~~~~
                         BsaI
                       ~~~~~~
              MetValSerGly ProArgHis GlyAspGly
    1 GGAATTCCAT ATGGTCTCAG GTCCGCGTCA TGGTGACGGT
      CCTTAAGGTA TACCAGAGTC CAGGCGCAGT ACCACTGCCA

SerPheSerAsp GluMetAsn ThrIleLeu AspAsnLeuAla·
   41 TCTTTCTCTG ACGAAATGAA CACCATCCTG GACAACCTGG
      AGAAAGAGAC TGCTTTACTT GTGGTAGGAC CTGTTGGACC

PmlI
          ~~~~~~
      ·AAlaArgAsp PheIleAsn TrpLeuIleGln ThrLysIle·
   81 CTGCACGTGA CTTCATCAAC TGGCTGATCC AGACCAAAAT
      GACGTGCACT GAAGTAGTTG ACCGACTAGG TCTGGTTTTA

BsaI                    BamHI
                  ~~~~~~                   ~~~~~~
      ·ThrAspPro ValSerGlyPro Arg
  121 CACCGACCCG GTCTCAGGTC CGCGCTAATG AGGATCCGCG
      GTGGCTGGGC CAGAGTCCAG GCGCGATTAC TCCTAGGCGC
```

```
  1 TGGCGAATGG GACGCGCCCT GTAGCGGCGC ATTAAGCGCG
    ACCGCTTACC CTGCGCGGGA CATCGCCGCG TAATTCGCGC
 41 GCGGGTGTGG TGGTTACGCG CAGCGTGACC GCTACACTTG
    CGCCCACACC ACCAATGCGC GTCGCACTGG CGATGTGAAC
 81 CCAGCGCCCT AGCGCCCGCT CCTTTCGCTT TCTTCCCTTC
    GGTCGCGGGA TCGCGGGCGA GGAAAGCGAA AGAAGGGAAG
121 CTTTCTCGCC ACGTTCGCCG GCTTTCCCCG TCAAGCTCTA
    GAAAGAGCGG TGCAAGCGGC CGAAGGGGC AGTTCGAGAT
161 AATCGGGGC TCCCTTTAGG GTTCCGATTT AGTGCTTTAC
    TTAGCCCCCG AGGGAAATCC CAAGGCTAAA TCACGAAATG
201 GGCACCTCGA CCCCAAAAAA CTTGATTAGG GTGATGGTTC
    CCGTGGAGCT GGGGTTTTTT GAACTAATCC CACTACCAAG
241 ACGTAGTGGG CCATCGCCCT GATAGACGGT TTTTCGCCCT
    TGCATCACCC GGTAGCGGGA CTATCTGCCA AAAAGCGGGA
281 TTGACGTTGG AGTCCACGTT CTTTAATAGT GGACTCTTGT
    AACTGCAACC TCAGGTGCAA GAAATTATCA CCTGAGAACA
321 TCCAAACTGG AACAACACTC AACCCTATCT CGGTCTATTC
    AGGTTTGACC TTGTTGTGAG TTGGGATAGA GCCAGATAAG
361 TTTTGATTTA TAAGGGATTT GCCGATTTC GGCCTATTGG
    AAAACTAAAT ATTCCCTAAA ACGGCTAAAG CCGGATAACC
401 TTAAAAAATG AGCTGATTTA ACAAAAATTT AACGCGAATT
    AATTTTTTAC TCGACTAAAT TGTTTTTAAA TTGCGCTTAA
441 TTAACAAAAT ATTAACGTTT ACAATTTCAG GTGGCACTTT
    AATTGTTTTA TAATTGCAAA TGTTAAAGTC CACCGTGAAA
481 TCGGGGAAAT GTGCGCGGAA CCCCTATTTG TTTATTTTTC
    AGCCCCTTTA CACGCGCCTT GGGGATAAAC AAATAAAAG
521 TAAATACATT CAAATATGTA TCCGCTCATG AATTAATTCT
    ATTTATGTAA GTTTATACAT AGGCGAGTAC TTAATTAAGA
561 TAGAAAAACT CATCGAGCAT CAAATGAAAC TGCAATTTAT
    ATCTTTTTGA GTAGCTCGTA GTTTACTTTG ACGTTAAATA
601 TCATATCAGG ATTATCAATA CCATATTTTT GAAAAAGCCG
    AGTATAGTCC TAATAGTTAT GGTATAAAAA CTTTTTCGGC
641 TTTCTGTAAT GAAGGAGAAA ACTCACCGAG GCAGTTCCAT
    AAAGACATTA CTTCCTCTTT TGAGTGGCTC CGTCAAGGTA
681 AGGATGGCAA GATCCTGGTA TCGGTCTGCG ATTCCGACTC
    TCCTACCGTT CTAGGACCAT AGCCAGACGC TAAGGCTGAG
721 GTCCAACATC AATACAACCT ATTAATTTCC CCTCGTCAAA
    CAGGTTGTAG TTATGTTGGA TAATTAAAGG GGAGCAGTTT
761 AATAAGGTTA TCAAGTGAGA AATCACCATG AGTGACGACT
    TTATTCCAAT AGTTCACTCT TTAGTGGTAC TCACTGCTGA
801 GAATCCGGTG AGAATGGCAA AAGTTTATGC ATTTCTTTCC
    CTTAGGCCAC TCTTACCGTT TTCAAATACG TAAAGAAAGG
841 AGACTTGTTC AACAGGCCAG CCATTACGCT CGTCATCAAA
```

Figure 4B

```
          TCTGAACAAG TTGTCCGGTC GGTAATGCGA GCAGTAGTTT
     881  ATCACTCGCA TCAACCAAAC CGTTATTCAT TCGTGATTGC
          TAGTGAGCGT AGTTGGTTTG CAATAAGTA AGCACTAACG
     921  GCCTGAGCGA GACGAAATAC GCGATCGCTG TTAAAAGGAC
          CGGACTCGCT CTGCTTTATG CGCTAGCGAC AATTTTCCTG
     961  AATTACAAAC AGGAATCGAA TGCAACCGGC GCAGGAACAC
          TTAATGTTTG TCCTTAGCTT ACGTTGGCCG CGTCCTTGTG
    1001  TGCCAGCGCA TCAACAATAT TTTCACCTGA ATCAGGATAT
          ACGGTCGCGT AGTTGTTATA AAAGTGGACT TAGTCCTATA
    1041  TCTTCTAATA CCTGGAATGC TGTTTTCCCG GGGATCGCAG
          AGAAGATTAT GGACCTTACG ACAAAGGGC CCCTAGCGTC
    1081  TGGTGAGTAA CCATGCATCA TCAGGAGTAC GGATAAAATG
          ACCACTCATT GGTACGTAGT AGTCCTCATG CCTATTTTAC
    1121  CTTGATGGTC GGAAGAGGCA TAAATTCCGT CAGCCAGTTT
          GAACTACCAG CCTTCTCCGT ATTTAAGGCA GTCGGTCAAA
    1161  AGTCTGACCA TCTCATCTGT AACATCATTG CAACGCTAC
          TCAGACTGGT AGAGTAGACA TTGTAGTAAC CGTTGCGATG
    1201  CTTTGCCATG TTTCAGAAAC AACTCTGGCG CATCGGGCTT
          GAAACGGTAC AAAGTCTTTG TTGAGACCGC GTAGCCCGAA
    1241  CCCATACAAT CGATAGATTG TCGCACCTGA TTGCCCGACA
          GGGTATGTTA GCTATCTAAC AGCGTGGACT AACGGGCTGT
    1281  TTATCGCGAG CCCATTTATA CCCATATAAA TCAGCATCCA
          AATAGCGCTC GGGTAAATAT GGGTATATTT AGTCGTAGGT
    1321  TGTTGGAATT TAATCGCGGC CTAGAGCAAG ACGTTTCCCG
          ACAACCTTAA ATTAGCGCCG GATCTCGTTC TGCAAAGGGC
    1361  TTGAATATGG CTCATAACAC CCCTTGTATT ACTGTTTATG
          AACTTATACC GAGTATTGTG GGGAACATAA TGACAAATAC
    1401  TAAGCAGACA GTTTATTGT TCATGACCAA AATCCCTTAA
          ATTCGTCTGT CAAATAACA AGTACTGGTT TTAGGGAATT
    1441  CGTGAGTTTT CGTTCCACTG AGCGTCAGAC CCCGTAGAAA
          GCACTCAAAA GCAAGGTGAC TCGCAGTCTG GGGCATCTTT
    1481  AGATCAAAGG ATCTTCTTGA GATCCTTTTT TTCTGCGCGT
          TCTAGTTTCC TAGAAGAACT CTAGGAAAAA AGACGCGCA
    1521  AATCTGCTGC TTGCAAACAA AAAACCACC GCTACCAGCG
          TTAGACGACG AACGTTTGTT TTTTGGTGG CGATGGTCGC
    1561  GTGGTTTGTT TGCCGGATCA AGAGCTACCA ACTCTTTTTC
          CACCAAACAA ACGGCCTAGT TCTCGATGGT TGAGAAAAG
    1601  CGAAGGTAAC TGGCTTCAGC AGAGCGCAGA TACCAAATAC
          GCTTCCATTG ACCGAAGTCG TCTCGCGTCT ATGGTTTATG
    1641  TGTCCTTCTA GTGTAGCCGT AGTTAGGCCA CCACTTCAAG
          ACAGGAAGAT CACATCGGCA TCAATCCGGT GGTGAAGTTC
    1681  AACTCTGTAG CACCGCCTAC ATACCTCGCT CTGCTAATCC
          TTGAGACATC GTGGCGGATG TATGGAGCGA GACGATTAGG
    1721  TGTTACCAGT GGCTGCTGCC AGTGGCGATA AGTCGTGTCT
          ACAATGGTCA CCGACGACGG TCACCGCTAT TCAGCACAGA
    1761  TACCGGGTTG GACTCAAGAC GATAGTTACC GGATAAGGCG
          ATGGCCCAAC CTGAGTTCTG CTATCAATGG CCTATTCCGC
```

Figure 4C

```
1801 CAGCGGTCGG GCTGAACGGG GGGTTCGTGC ACACAGCCCA
     GTCGCCAGCC CGACTTGCCC CCCAAGCACG TGTGTCGGGT
1841 GCTTGGAGCG AACGACCTAC ACCGAACTGA GATACCTACA
     CGAACCTCGC TTGCTGGATG TGGCTTGACT CTATGGATGT
1881 GCGTGAGCTA TGAGAAAGCG CCACGCTTCC CGAAGGGAGA
     CGCACTCGAT ACTCTTTCGC GGTGCGAAGG GCTTCCCTCT
1921 AAGGCGGACA GGTATCCGGT AAGCGGCAGG GTCGGAACAG
     TTCCGCCTGT CCATAGGCCA TTCGCCGTCC CAGCCTTGTC
1961 GAGAGCGCAC GAGGGAGCTT CCAGGGGGAA ACGCCTGGTA
     CTCTCGCGTG CTCCCTCGAA GGTCCCCCTT TGCGGACCAT
2001 TCTTTATAGT CCTGTCGGGT TTCGCCACCT CTGACTTGAG
     AGAAATATCA GGACAGCCCA AAGCGGTGGA GACTGAACTC
2041 CGTCGATTTT TGTGATGCTC GTCAGGGGGG CGGAGCCTAT
     GCAGCTAAAA ACACTACGAG CAGTCCCCCC GCCTCGGATA
2081 GGAAAAACGC CAGCAACGCG GCCTTTTTAC GGTTCCTGGC
     CCTTTTTGCG GTCGTTGCGC CGGAAAAATG CCAAGGACCG
2121 CTTTTGCTGG CCTTTTGCTC ACATGTTCTT TCCTGCGTTA
     GAAAACGACC GGAAAACGAG TGTACAAGAA AGGACGCAAT
2161 TCCCCTGATT CTGTGGATAA CCGTATTACC GCCTTTGAGT
     AGGGGACTAA GACACCTATT GGCATAATGG CGGAAACTCA
2201 GAGCTGATAC CGCTCGCCGC AGCCGAACGA CCGAGCGCAG
     CTCGACTATG GCGAGCGGCG TCGGCTTGCT GGCTCGCGTC
2241 CGAGTCAGTG AGCGAGGAAG CGGAAGAGCG CCTGATGCGG
     GCTCAGTCAC TCGCTCCTTC GCCTTCTCGC GGACTACGCC
2281 TATTTTCTCC TTACGCATCT GTGCGGTATT TCACACCGCA
     ATAAAAGAGG AATGCGTAGA CACGCCATAA AGTGTGGCGT
2321 TATATGGTGC ACTCTCAGTA CAATCTGCTC TGATGCCGCA
     ATATACCACG TGAGAGTCAT GTTAGACGAG ACTACGGCGT
2361 TAGTTAAGCC AGTATACACT CCGCTATCGC TACGTGACTG
     ATCAATTCGG TCATATGTGA GGCGATAGCG ATGCACTGAC
2401 GGTCATGGCT GCGCCCCGAC ACCCGCCAAC ACCCGCTGAC
     CCAGTACCGA CGCGGGCTG TGGGCGGTTG TGGGCGACTG
2441 GCGCCCTGAC GGGCTTGTCT GCTCCCGGCA TCCGCTTACA
     CGCGGGACTG CCCGAACAGA CGAGGGCCGT AGGCGAATGT
2481 GACAAGCTGT GACCGTCTCC GGGAGCTGCA TGTGTCAGAG
     CTGTTCGACA CTGGCAGAGG CCCTCGACGT ACACAGTCTC
2521 GTTTTCACCG TCATCACCGA AACGCGCGAG GCAGCTGCGG
     CAAAAGTGGC AGTAGTGGCT TTGCGCGCTC CGTCGACGCC
2561 TAAAGCTCAT CAGCGTGGTC GTGAAGCGAT TCACAGATGT
     ATTTCGAGTA GTCGCACCAG CACTTCGCTA AGTGTCTACA
2601 CTGCCTGTTC ATCCGCGTCC AGCTCGTTGA GTTTCTCCAG
     GACGGACAAG TAGGCGCAGG TCGAGCAACT CAAAGAGGTC
2641 AAGCGTTAAT GTCTGGCTTC TGATAAAGCG GGCCATGTTA
     TTCGCAATTA CAGACCGAAG ACTATTTCGC CCGGTACAAT
2681 AGGGCGGTTT TTTCCTGTTT GGTCACTGAT GCCTCCGTGT
     TCCCGCCAAA AAAGGACAAA CCAGTGACTA CGGAGGCACA
2721 AAGGGGGATT TCTGTTCATG GGGGTAATGA TACCGATGAA
```

Figure 4D

```
      TTCCCCCTAA AGACAAGTAC CCCCATTACT ATGGCTACTT
2761  ACGAGAGAGG ATGCTCACGA TACGGGTTAC TGATGATGAA
      TGCTCTCTCC TACGAGTGCT ATGCCCAATG ACTACTACTT
2801  CATGCCCGGT TACTGGAACG TTGTGAGGGT AAACAACTGG
      GTACGGGCCA ATGACCTTGC AACACTCCCA TTTGTTGACC
2841  CGGTATGGAT GCGGCGGGAC CAGAGAAAAA TCACTCAGGG
      GCCATACCTA CGCCGCCCTG GTCTCTTTTT AGTGAGTCCC
2881  TCAATGCCAG CGCTTCGTTA ATACAGATGT AGGTGTTCCA
      AGTTACGGTC GCGAAGCAAT TATGTCTACA TCCACAAGGT
2921  CAGGGTAGCC AGCAGCATCC TGCGATGCAG ATCCGGAACA
      GTCCATCGG TCGTCGTAGG ACGCTACGTC TAGGCCTTGT
2961  TAATGGTGCA GGGCGCTGAC TTCCGCGTTT CCAGACTTTA
      ATTACCACGT CCCGCGACTG AAGGCGCAAA GGTCTGAAAT
3001  CGAAACACGG AAACCGAAGA CCATTCATGT TGTTGCTCAG
      GCTTTGTGCC TTTGGCTTCT GGTAAGTACA ACAACGAGTC
3041  GTCGCAGACG TTTTGCAGCA GCAGTCGCTT CACGTTCGCT
      CAGCGTCTGC AAAACGTCGT CGTCAGCGAA GTGCAAGCGA
3081  CGCGTATCGG TGATTCATTC TGCTAACCAG TAAGGCAACC
      GCGCATAGCC ACTAAGTAAG ACGATTGGTC ATTCCGTTGG
3121  CCGCCAGCCT AGCCGGGTCC TCAACGACAG GAGCACGATC
      GGCGGTCGGA TCGGCCCAGG AGTTGCTGTC CTCGTGCTAG
3161  ATGCGCACCC GTGGGGCCGC CATGCCGGCG ATAATGGCCT
      TACGCGTGGG CACCCCGGCG GTACGGCCGC TATTACCGGA
3201  GCTTCTCGCC GAAACGTTTG GTGGCGGGAC CAGTGACGAA
      CGAAGAGCGG CTTTGCAAAC CACCGCCCTG GTCACTGCTT
3241  GGCTTGAGCG AGGGCGTGCA AGATTCCGAA TACCGCAAGC
      CCGAACTCGC TCCCGCACGT TCTAAGGCTT ATGGCGTTCG
3281  GACAGGCCGA TCATCGTCGC GCTCCAGCGA AAGCGGTCCT
      CTGTCCGGCT AGTAGCAGCG CGAGGTCGCT TTCGCCAGGA
3321  CGCCGAAAAT GACCCAGAGC GCTGCCGGCA CCTGTCCTAC
      GCGGCTTTTA CTGGGTCTCG CGACGGCCGT GGACAGGATG
3361  GAGTTGCATG ATAAAGAAGA CAGTCATAAG TGCGGCGACG
      CTCAACGTAC TATTTCTTCT GTCAGTATTC ACGCCGCTGC
3401  ATAGTCATGC CCCGCGCCCA CCGGAAGGAG CTGACTGGGT
      TATCAGTACG GGGCGCGGGT GGCCTTCCTC GACTGACCCA
3441  TGAAGGCTCT CAAGGGCATC GGTCGAGATC CCGGTGCCTA
      ACTTCCGAGA GTTCCCGTAG CCAGCTCTAG GGCCACGGAT
3481  ATGAGTGAGC TAACTTACAT TAATTGCGTT GCGCTCACTG
      TACTCACTCG ATTGAATGTA ATTAACGCAA CGCGAGTGAC
3521  CCCGCTTTCC AGTCGGGAAA CCTGTCGTGC CAGCTGCATT
      GGGCGAAAGG TCAGCCCTTT GGACAGCACG GTCGACGTAA
3561  AATGAATCGG CCAACGCGCG GGGAGAGGCG GTTTGCGTAT
      TTACTTAGCC GGTTGCGCGC CCCTCTCCGC CAAACGCATA
3601  TGGGCGCCAG GGTGGTTTTT CTTTTCACCA GTGAGACGGG
      ACCCGCGGTC CCACCAAAAA GAAAAGTGGT CACTCTGCCC
3641  CAACAGCTGA TTGCCCTTCA CCGCCTGGCC CTGAGAGAGT
      GTTGTCGACT AACGGGAAGT GGCGGACCGG GACTCTCTCA
```

Figure 4E

```
3681  TGCAGCAAGC  GGTCCACGCT  GGTTTGCCCC  AGCAGGCGAA
      ACGTCGTTCG  CCAGGTGCGA  CCAAACGGGG  TCGTCCGCTT
3721  AATCCTGTTT  GATGGTGGTT  AACGGCGGGA  TATAACATGA
      TTAGGACAAA  CTACCACCAA  TTGCCGCCCT  ATATTGTACT
3761  GCTGTCTTCG  GTATCGTCGT  ATCCCACTAC  CGAGATGTCC
      CGACAGAAGC  CATAGCAGCA  TAGGGTGATG  GCTCTACAGG
3801  GCACCAACGC  GCAGCCCGGA  CTCGGTAATG  GCGCGCATTG
      CGTGGTTGCG  CGTCGGGCCT  GAGCCATTAC  CGCGCGTAAC
3841  CGCCCAGCGC  CATCTGATCG  TTGGCAACCA  GCATCGCAGT
      GCGGGTCGCG  GTAGACTAGC  AACCGTTGGT  CGTAGCGTCA
3881  GGGAACGATG  CCCTCATTCA  GCATTTGCAT  GGTTTGTTGA
      CCCTTGCTAC  GGGAGTAAGT  CGTAAACGTA  CCAAACAACT
3921  AAACCGGACA  TGGCACTCCA  GTCGCCTTCC  CGTTCCGCTA
      TTTGGCCTGT  ACCGTGAGGT  CAGCGGAAGG  GCAAGGCGAT
3961  TCGGCTGAAT  TTGATTGCGA  GTGAGATATT  TATGCCAGCC
      AGCCGACTTA  AACTAACGCT  CACTCTATAA  ATACGGTCGG
4001  AGCCAGACGC  AGACGCGCCG  AGACAGAACT  TAATGGGCCC
      TCGGTCTGCG  TCTGCGCGGC  TCTGTCTTGA  ATTACCCGGG
4041  GCTAACAGCG  CGATTTGCTG  GTGACCCAAT  GCGACCAGAT
      CGATTGTCGC  GCTAAACGAC  CACTGGGTTA  CGCTGGTCTA
4081  GCTCCACGCC  CAGTCGCGTA  CCGTCTTCAT  GGGAGAAAAT
      CGAGGTGCGG  GTCAGCGCAT  GGCAGAAGTA  CCCTCTTTTA
4121  AATACTGTTG  ATGGGTGTCT  GGTCAGAGAC  ATCAAGAAAT
      TTATGACAAC  TACCCACAGA  CCAGTCTCTG  TAGTTCTTTA
4161  AACGCCGGAA  CATTAGTGCA  GGCAGCTTCC  ACAGCAATGG
      TTGCGGCCTT  GTAATCACGT  CCGTCGAAGG  TGTCGTTACC
4201  CATCCTGGTC  ATCCAGCGGA  TAGTTAATGA  TCAGCCCACT
      GTAGGACCAG  TAGGTCGCCT  ATCAATTACT  AGTCGGGTGA
4241  GACGCGTTGC  GCGAGAAGAT  TGTGCACCGC  CGCTTTACAG
      CTGCGCAACG  CGCTCTTCTA  ACACGTGGCG  GCGAAATGTC
4281  GCTTCGACGC  CGCTTCGTTC  TACCATCGAC  ACCACCACGC
      CGAAGCTGCG  GCGAAGCAAG  ATGGTAGCTG  TGGTGGTGCG
4321  TGGCACCCAG  TTGATCGGCG  CGAGATTTAA  TCGCCGCGAC
      ACCGTGGGTC  AACTAGCCGC  GCTCTAAATT  AGCGGCGCTG
4361  AATTTGCGAC  GGCGCGTGCA  GGGCCAGACT  GGAGGTGGCA
      TTAAACGCTG  CCGCGCACGT  CCCGGTCTGA  CCTCCACCGT
4401  ACGCCAATCA  GCAACGACTG  TTTGCCCGCC  AGTTGTTGTG
      TGCGGTTAGT  CGTTGCTGAC  AAACGGGCGG  TCAACAACAC
4441  CCACGCGGTT  GGGAATGTAA  TTCAGCTCCG  CCATCGCCGC
      GGTGCGCCAA  CCCTTACATT  AAGTCGAGGC  GGTAGCGGCG
4481  TTCCACTTTT  TCCCGCGTTT  TCGCAGAAAC  GTGGCTGGCC
      AAGGTGAAAA  AGGGCGCAAA  AGCGTCTTTG  CACCGACCGG
4521  TGGTTCACCA  CGCGGGAAAC  GGTCTGATAA  GAGACACCGG
      ACCAAGTGGT  GCGCCCTTTG  CCAGACTATT  CTCTGTGGCC
4561  CATACTCTGC  GACATCGTAT  AACGTTACTG  GTTTCACATT
      GTATGAGACG  CTGTAGCATA  TTGCAATGAC  CAAAGTGTAA
4601  CACCACCCTG  AATTGACTCT  CTTCCGGGCG  CTATCATGCC
```

Figure 4F

```
        GTGGTGGGAC  TTAACTGAGA  GAAGGCCCGC  GATAGTACGG
4641    ATACCGCGAA  AGGTTTTGCG  CCATTCGATG  GTGTCCGGGA
        TATGGCGCTT  TCCAAAACGC  GGTAAGCTAC  CACAGGCCCT
4681    TCTCGACGCT  CTCCCTTATG  CGACTCCTGC  ATTAGGAAGC
        AGAGCTGCGA  GAGGGAATAC  GCTGAGGACG  TAATCCTTCG
4721    AGCCCAGTAG  TAGGTTGAGG  CCGTTGAGCA  CCGCCGCCGC
        TCGGGTCATC  ATCCAACTCC  GGCAACTCGT  GGCGGCGGCG
4761    AAGGAATGGT  GCATGCAAGG  AGATGGCGCC  CAACAGTCCC
        TTCCTTACCA  CGTACGTTCC  TCTACCGCGG  GTTGTCAGGG
4801    CCGGCCACGG  GGCCTGCCAC  CATACCCACG  CCGAAACAAG
        GGCCGGTGCC  CCGGACGGTG  GTATGGGTGC  GGCTTTGTTC
4841    CGCTCATGAG  CCCGAAGTGG  CGAGCCCGAT  CTTCCCCATC
        GCGAGTACTC  GGGCTTCACC  GCTCGGGCTA  GAAGGGGTAG
4881    GGTGATGTCG  GCGATATAGG  CGCCAGCAAC  CGCACCTGTG
        CCACTACAGC  CGCTATATCC  GCGGTCGTTG  GCGTGGACAC
4921    GCGCCGGTGA  TGCCGGCCAC  GATGCGTCCG  GCGTAGAGGA
        CGCGGCCACT  ACGGCCGGTG  CTACGCAGGC  CGCATCTCCT
4961    TCGAGATCGA  TCTCGATCCC  GCGAATTAA   TACGACTCAC
        AGCTCTAGCT  AGAGCTAGGG  CGCTTAATT   ATGCTGAGTG
5001    TATAGGGGAA  TTGTGAGCGG  ATAACAATTC  CCCTCTAGAA
        ATATCCCCTT  AACACTCGCC  TATTGTTAAG  GGGAGATCTT
                                            NdeI
                                            ~~~~~~
                                            BsaI
                                            ~~~
                                            MetVal·
5041    ATAATTTTGT  TTAACTTTAA  GAAGGAGATA  TACAT*ATGGT*
        TATTAAAACA  AATTGAAATT  CTTCCTCTAT  ATGTA*TACCA*
        BsaI
        ~~~
        ·SerGlyPro  ArgHisGlyAsp  GlySerPhe  SerAspGlu
5081    *CTCAGGTCCG*  *CGTCATGGTG*  *ACGGTTCTTT*  *CTCTGACGAA*
        *GAGTCCAGGC*  *GCAGTACCAC*  *TGCCAAGAAA*  *GAGACTGCTT*
                                    PmlI
                                    ~~~~~~
        MetAsnThrIle  LeuAspAsn  LeuAlaAla  ArgAspPheIle·
5121    ATGAACACCA  TCCTGGACAA  CCTGGCTGCA  CGTGACTTCA
        TACTTGTGGT  AGGACCTGTT  GGACCGACGT  GCACTGAAGT
                                                BsaI
                                                ~~~~~~
        ·IAsnTrpLeu  IleGlnThr  LysIleThrAsp  ProValSer·
5161    TCAACTGGCT  GATCCAGACC  AAAATCACCG  ACCCGGTCTC
        AGTTGACCGA  CTAGGTCTGG  TTTTAGTGGC  TGGGCCAGAG
        ·GlyProArg  HisGlyAspGly  SerPheSer  AspGluMet
5201    *AGGTCCGCGT*  CATGGTGACG  GTTCTTTCTC  TGACGAAATG
        *TCCAGGCGCA*  GTACCACTGC  CAAGAAAGAG  ACTGCTTTAC
                                            PmlI
```

Figure 4G

```
         AsnThrIleLeu AspAsnLeu AlaAlaArg AspPheIleAsn·
5241     AACACCATCC TGGACAACCT GGCTGCACGT GACTTCATCA
         TTGTGGTAGG ACCTGTTGGA CCGACGTGCA CTGAAGTAGT
                                              BsaI

·ATrpLeuIle GlnThrLys IleThrAspPro ValSerGly·
5281     ACTGGCTGAT CCAGACCAAA ATCACCGACC CGGTCTCAGG
         TGACCGACTA GGTCTGGTTT TAGTGGCTGG GCCAGAGTCC
         ·ProArgHis GlyAspGlySer PheSerAsp GluMetAsn
5321     TCCGCGTCAT GGTGACGGTT CTTTCTCTGA CGAAATGAAC
         AGGCGCAGTA CCACTGCCAA GAAAGAGACT GCTTTACTTG
                                       PmlI

ThrIleLeuAsp AsnLeuAla AlaArgAsp PheIleAsnTrp·
5361     ACCATCCTGG ACAACCTGGC TGCACGTGAC TTCATCAACT
         TGGTAGGACC TGTTGGACCG ACGTGCACTG AAGTAGTTGA
                                              BsaI

·TLeuIleGln ThrLysIle ThrAspProVal SerGlyPro·
5401     GGCTGATCCA GACCAAAATC ACCGACCCGG TCTCAGGTCC
         CCGACTAGGT CTGGTTTTAG TGGCTGGGCC AGAGTCCAGG
         ·ArgHisGly AspGlySerPhe SerAspGlu MetAsnThr
5441     GCGTCATGGT GACGGTTCTT TCTCTGACGA AATGAACACC
         CGCAGTACCA CTGCCAAGAA AGAGACTGCT TTACTTGTGG
                                       PmlI

IleLeuAspAsn LeuAlaAla ArgAspPhe IleAsnTrpLeu·
5481     ATCCTGGACA ACCTGGCTGC ACGTGACTTC ATCAACTGGC
         TAGGACCTGT TGGACCGACG TGCACTGAAG TAGTTGACCG
                                              BsaI

·LIleGlnThr LysIleThr AspProValSer GlyProArg·
5521     TGATCCAGAC CAAAATCACC GACCCGGTCT CAGGTCCGCG
         ACTAGGTCTG GTTTTAGTGG CTGGGCCAGA GTCCAGGCGC
         ·HisGlyAsp GlySerPheSer AspGluMet AsnThrIle
5561     TCATGGTGAC GGTTCTTTCT CTGACGAAAT GAACACCATC
         AGTACCACTG CCAAGAAAGA GACTGCTTTA CTTGTGGTAG
                                       PmlI

LeuAspAsnLeu AlaAlaArg AspPheIle AsnTrpLeuIle·
5601     CTGGACAACC TGGCTGCACG TGACTTCATC AACTGGCTGA
         GACCTGTTGG ACCGACGTGC ACTGAAGTAG TTGACCGACT
                                              BsaI

·IGlnThrLys IleThrAsp ProValSerGly ProArgHis·
5641     TCCAGACCAA AATCACCGAC CGGTCTCAG GTCCGCGTCA
```

Figure 4H

```
           AGGTCTGGTT TTAGTGGCTG GGCCAGAGTC CAGGCGCAGT
           ·GlyAspGly SerPheSerAsp GluMetAsn ThrIleLeu
     5681  TGGTGACGGT TCTTTCTCTG ACGAAATGAA CACCATCCTG
           ACCACTGCCA AGAAAGAGAC TGCTTTACTT GTGGTAGGAC
                                 PmlI
                                 ~~~~~
            AspAsnLeuAla AlaArgAsp PheIleAsn TrpLeuIleGln·
     5721  GACAACCTGG CTGCACGTGA CTTCATCAAC TGGCTGATCC
           CTGTTGGACC GACGTGCACT GAAGTAGTTG ACCGACTAGG
                                 BsaI
                                 ~~~~~
           ·GThrLysIle ThrAspPro ValSerGlyPro Arg
     5761  AGACCAAAAT CACCGACCCG GTCTCAGGTC CGCGCTAATG
           TCTGGTTTTA GTGGCTGGGC CAGAGTCCAG GCGCGATTAC

BamHI
           ~~~~~
     5801  AGGATCCGAA TTCGAGCTCC GTCGACAAGC TTGCGGCCGC
           TCCTAGGCTT AAGCTCGAGG CAGCTGTTCG AACGCCGGCG
     5841  ACTCGAGCAC CACCACCACC ACCACTGAGA TCCGGCTGCT
           TGAGCTCGTG GTGGTGGTGG TGGTGACTCT AGGCCGACGA
     5881  AACAAAGCCC GAAAGGAAGC TGAGTTGGCT GCTGCCACCG
           TTGTTTCGGG CTTTCCTTCG ACTCAACCGA CGACGGTGGC
     5921  CTGAGCAATA ACTAGCATAA CCCCTTGGGG CCTCTAAACG
           GACTCGTTAT TGATCGTATT GGGGAACCCC GGAGATTTGC
     5961  GGTCTTGAGG GGTTTTTGC TGAAGGAGG AACTATATCC
           CCAGAACTCC CCAAAAAACG ACTTCCTCC TTGATATAGG
     6001  GGAT
           CCTA
```

PRODUCTION OF GLUCAGON-LIKE PEPTIDE 2

FIELD OF THE INVENTION

This invention applies the art of molecular biology in the field of protein production. More particularly, the invention relates to the production of recombinant glucagon-like peptide 2, or GLP-2, and analogs thereof.

BACKGROUND OF THE INVENTION

GLP-2 is a 33 amino acid product of the proglucagon gene. Recent evidence indicates that GLP-2 promotes nutrient absorption via expansion of the mucosal epithelium by stimulation of crypt cell proliferation and inhibition of apoptosis in the small intestine. GLP-2 also reduces epithelial permeability, and decreases meal-stimulated gastric acid secretion and gastrointestinal mobility. Many of these effects have been attributed not only to the wild type peptide, but also to analogs thereof, including particularly those rendered resistant to digestion by serum-borne enzymes, such as DPP-IV, by substitution of the alanine resident at position 2 with, for instance, glycine. A variety of bioactive GLP-2 analogs are described, for instance, in U.S. Pat. No. 5,789,379.

With recent recognition of its pharmaceutical properties, there is a demand for large quantities of GLP-2 and analogs thereof to permit development and subsequent medical use of these products. Solid or solution phase synthetic methods have typically been applied to produce the research quantities of GLP-2 and analogs used to date. The production of GLP-2 as a recombinant product of genetically engineered hosts has been suggested, for instance in U.S. Pat. Nos. 5,789,379 and 6,287,806, and is described in U.S. Pat. No. 5,629,205. However, prior art production systems have limitations in terms of product yield and quality, and it would be desirable to provide a system that yields quality GLP-2 peptide in a cost-effective manner.

It is accordingly an object of the present invention to provide a process, and intermediates and reagents useful therein, by which commercial quantities of GLP-2 can be produced.

It is another object of the present invention to provide GLP-2 and analogs thereof, particularly the [Gly$^2$]hGLP-2 analog, in structurally authentic form.

SUMMARY OF THE INVENTION

In accordance with the present invention, there is provided a process by which GLP-2 and analogs thereof are produced not only in relatively high yield, but also as structurally authentic products, comprising only the natural form of the naturally occurring amino acids in the sequence constituting the GLP-2 peptide. Preferably, the N- and C-terminal residues are "terminally authentic". In particular, the present process yields the desired GLP-2 as a peptide having N- and C-terminal residues that are without residual amino acids and other chemical moieties that often result from recombinant methods of protein production, particularly those which rely on production of the protein as a fused precursor from which the target protein must be released.

More particularly, and according to one aspect of the present invention, there is provided a single chain polypeptide precursor in which two or more copies of the GLP-2 peptide are coupled tandemly through a linker that is cleavable to release each unit of GLP-2 peptide as a product having authentic N- and C-termini. In a particular embodiment of the invention, the GLP-2 peptides are coupled using a linker that presents cleavage sites at each of its flanks. In a specific embodiment, the linker presents an acid cleavage site at one flank, and an enzyme cleavage site at its other flank.

In another aspect, the present invention provides a process for producing a GLP-2 peptide having authentic N- and C-termini, in which the present GLP-2 peptide multimer is cleaved to release each GLP-2 peptide unit resident therein.

In other aspects of the present invention, there are further provided polynucleotides, genetic constructs, and transformed host cells useful in the production of such multimeric GLP-2 peptide precursors.

In still another aspect, the present invention provides [Gly$^2$]hGLP-2 as a recombinant product characterized by a mass essentially identical to theoretical mass. In a related aspect, the present invention provides a pharmaceutical composition comprising such peptide in a therapeutically useful amount and a pharmaceutically acceptable carrier Both the foregoing general description and the following brief description of the drawings and detailed description are exemplary and explanatory and are intended to provide further explanation of the invention as claimed. Other objects, advantages, and novel features will be readily apparent to those skilled in the art from the following detailed description of the invention.

BRIEF REFERENCE TO THE DRAWINGS

FIG. 1 illustrates PCR-based construction of a gene that encodes a [Gly$^2$]hGLP-2 unit flanked by a thrombin cleavage site (SEQ ID NO: 5 encodes SEQ ID NO: 6) and an acid cleavage site (SEQ ID NOS 7 and 8);

FIG. 2 illustrates the expected DNA sequence of the amplification product of FIG. 1 (SEQ ID NO: 3 encodes SEQ ID NO: 4). The sequence of the [Gly$^2$]hGLP-2 unit is underlined;

FIGS. 4A through 4H provides the nucleotide sequence of pKS58, carrying a construct encoding a [Gly$^2$]hGLP-2 hexamer, where the amino acid sequence is also illustrated, showing the GLP-2 peptide units in bold. Any reference hereafter to "FIG. 4" should be interpreted as a reference to FIGS. 4A through 4H.

Figure 3:
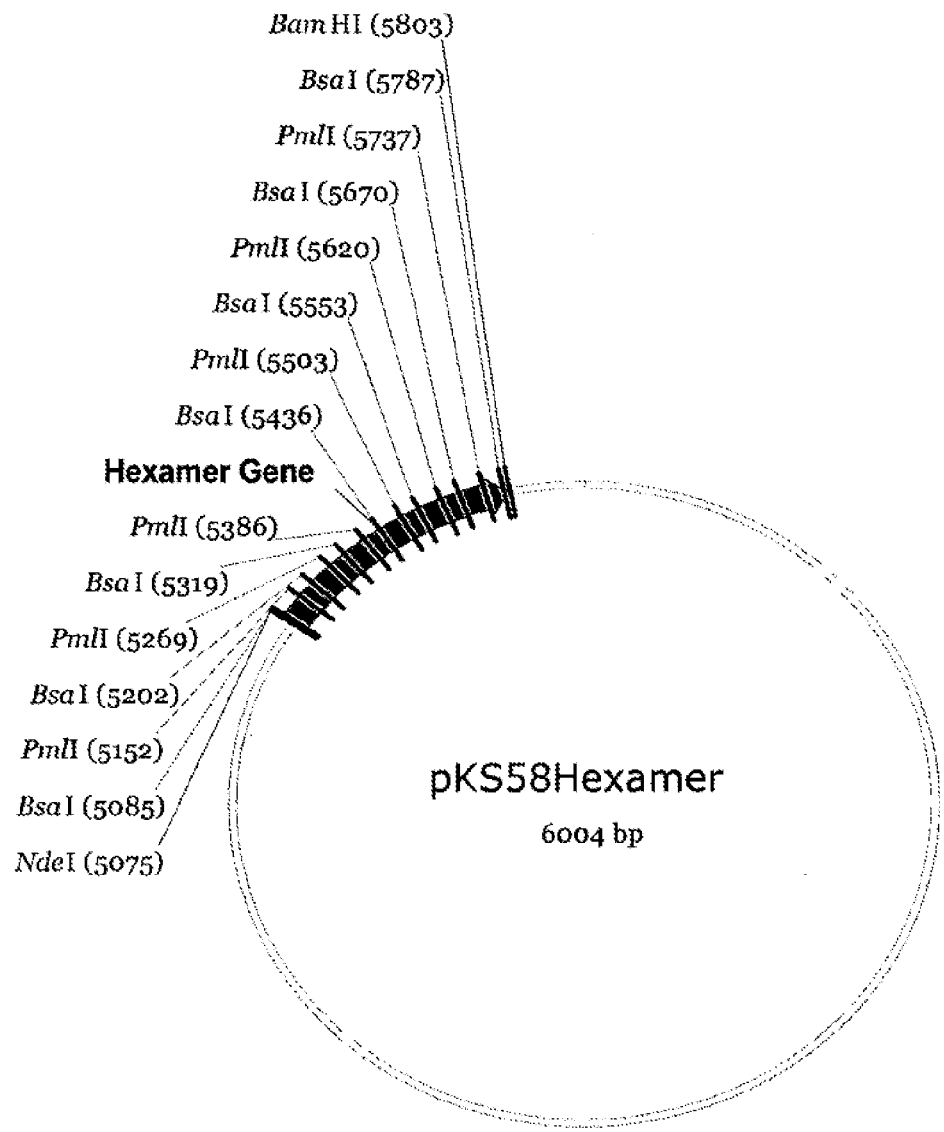
FIG. 3 is a plasmid map of pKS58 carrying a gene that encodes a [Gly$^2$]hGLP-2 hexamer.
Figure 5:
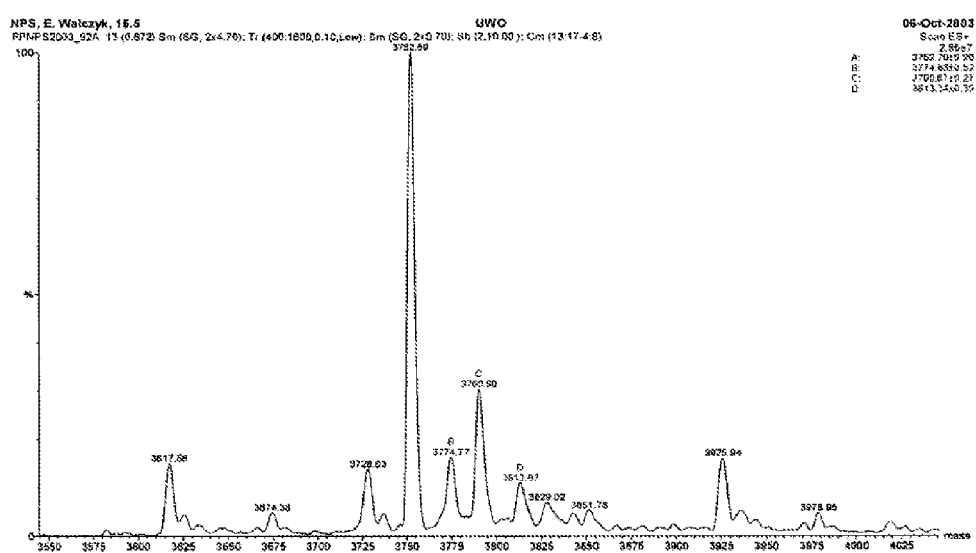

FIG. 5 provides a mass spectrometric analysis of a GLP-2 peptide produced as herein described.

DETAILED DESCRIPTION OF THE INVENTION

In one aspect, the present invention provides a genetic construct, in the form of a polynucleotide, adapted to produce the GLP-2 peptide as a single chain, multimeric precursor comprising at least two copies of a GLP-2 peptide. Each such peptide is coupled to the next through a linker having flanks that present cleavage sites permitting the release of the GLP-2 peptides as monomers having N- and C-termini that are authentic, and thus are essentially free from chemical residues originating from the linker or the cleavage process. As a recombinant product, the resulting GLP-2 peptide is also free from chemical moieties such as blocking groups used in solution and solid phase peptide synthesis.

In the present invention, GLP-2 peptide units within the multimer are coupled using a linker that presents cleavage sites at the N- and C-termini of the resident GLP-2 peptide units. These sites, and the agents used to cleave them, are selected so that the GLP-2 peptide remains intact during the cleavage process, so that isolation and purification yields a GLP-2 peptide having the desired N- and C-terminal residues without any requirement for further processing.

In a preferred embodiment of the present invention, the linker is a relatively short peptide sequence, consisting of not more than about 25 residues, desirably less than about 20 residues, suitably less than about 15 residues, and most suitably less than about 10 residues. The sequence of the linker is chosen to avoid formation of complex secondary structures that mask the linker to the chosen cleaving agent. The cleavage site presented by the linker can be a site that is vulnerable to cleavage by enzyme or chemical conditions such as pH.

In a preferred embodiment, the linker is desirably one that presents an enzyme cleavage site at one flank, and an acid cleavage site at another flank. The site sensitive to cleavage by enzyme can be any site that is not reproduced elsewhere in the GLP-2 peptide multimer and is cleaved by any enzyme not present otherwise during the manufacturing process. Enzymes suitable for such cleavage, and sequences recognized and cleaved by those enzymes, include enterokinase and the sequence Asp-Asp-Asp-Asp-Lys (SEQ ID NO: 9), and Factor Xa and the sequence Ile-Glu-Gly-Arg (SEQ ID NO: 10). In a preferred embodiment, the enzyme cleavage site is one cleaved by thrombin, and the thrombin cleavage sequence is ValSerGlyProArg (SEQ ID NO: 11).

An acid cleavage site presented in the GLP-2 peptide multimer is suitably the sequence Asp-Pro, which is cut under low pH conditions between the Asp and Pro residues.

In embodiments of the present invention, the linker provides, within the multimer, an acid cleavage site at its N-terminus and a thrombin cleavage site at its C-terminus. In a specific embodiment, the linker has the amino acid sequence ProValSerGlyProArg (SEQ ID NO: 12). Alternatively, it will be appreciated that the N-terminal Pro residue and the C-terminal thrombin cleavage site can be separated by additional amino acid sequence that does not detract from the vulnerability of the flanks to the desired cleavage conditions. When the noted particular linker is incorporated into the multimer, the GLP-2 peptide units are those that incorporate Asp as a C-terminal residue, and which otherwise lack both an acid cleavage site and a thrombin cleavage site. When linked between such GLP-2 peptide units, the N-terminal Pro residue of the linker, together with the C-terminal Asp residue of the upstream GLP-2 peptide unit, form the Asp-Pro site that is cleavable in acid, i.e., at low pH, to yield the authentic C-terminus of the GLP-2 peptide. Moreover, the linker sequence ValSerGlyProArg (SEQ ID NO: 11) presents a thrombin recognition sequence that is cleaved by thrombin on the C-terminal side of its Arg residue, to yield an authentic N-terminal residue in the GLP-2 peptide unit downstream thereof. While a specific thrombin cleavage sequence is shown, it will be understood that any equivalent sequence recognized and cleaved by thrombin can be incorporated in the linker, including those sequences reported by Chang, J. (1985) Eur. J. Biochem. 151, 217-224, incorporated herein by reference. It will also be appreciated that any GLP-2 peptide unit within the multimer should not incorporate any thrombin cleavage sequence within the primary structure of that GLP-2 unit.

Thus, in a valuable aspect of the present invention, there is provided a single chain polypeptide that incorporates at least two GLP-2 peptide units coupled tandemly through a linker having the sequence ProValSerGlyProArg (SEQ ID NO: 12), wherein the GLP-2 peptide incorporates a C-terminal Asp residue, and otherwise lacks both a thrombin cleavage sequence and an acid cleavage sequence.

In a preferred embodiment of this aspect of the present invention, the GLP-2 peptide unit incorporated within the multimer is the analog of human GLP-2 in which the Ala at position 2 is substituted by Gly, i.e., [Gly$^2$]hGLP-2, having the amino acid sequence illustrated in FIG. 2. In the alternative, the GLP-2 peptide can be the wild type human GLP-2 having the amino acid sequence reported by Buhl et al. in J. Biol. Chem., 1988, 263(18):8621, a homolog thereof, or any other analog thereof that retains a C-terminal Asp residue and is otherwise lacking in both thrombin and acid cleavage sites. Suitable analogs can be selected for instance from those described in co-assigned U.S. Pat. Nos. 5,789,379 and 6,184,201, the disclosures of which are incorporated herein by reference.

In other embodiments, the multimeric GLP-2 peptide precursor comprises at least two GLP-2 peptide units, and as many as 10 or more such units, e.g. up to about 30 units and more suitably up to about 20 units, linked in tandem through the noted linker. In specific embodiments, the number of units of GLP-2 peptide in the precursor is 2, 3, 4, 5, 6 or 7. In one preferred embodiment, the multimeric precursor incorporates six GLP-2 peptide units. In another preferred embodiment, the precursor incorporates seven GLP-2 peptide units.

It will be appreciated that the GLP-2 peptide multimer, for expression as a recombinant product, will incorporate an N-terminal extension that incorporates at least an initial Methionine residue. In embodiments, the N-terminal extension is incorporated as a carrier peptide that bears the N-terminal methionine residue and is cleavable from the multimer per se. The carrier peptide thus can be a secretion signal that is cleaved by the host in the process of secreting the mature multimer. Alternatively and desirably, the carrier peptide is not a secretion signal, and the multimeric product accumulates in the cytoplasm of the host where it is recovered optionally in the form of inclusion bodies. Where the carrier peptide is not designed to be removed by the host cell, the carrier peptide desirably further incorporates amino acids that constitute the same enzyme cleavage site presented within the multimer at the N-terminal flank of each GLP-2 peptide unit. In this arrangement, treatment of the expressed GLP-2 multimer with the selected enzyme not only cuts the carrier from the multimer, but also cuts the multimer at the N-terminus of each GLP-2 peptide unit resident therein. In one embodiment, the carrier peptide initiates with a Met residue and terminates with a thrombin cleavage site, such as ValSerGlyProArg (SEQ ID NO: 11). The N-terminal carrier peptide of the GLP-2 multimer can further incorporate other intervening sequences functional, for instance, in purification of the multimer such as the so-called His-Tag, in enhancing the level of expression of the multimer by the selected host, or in promoting formation of the multimer as inclusion bodies such as hydrophobic amino acid sequences.

It will also be appreciated that the GLP-2 peptide multimer can terminate with a GLP-2 peptide unit or, if desired, can terminate with a peptide extension thereof useful, for instance, in the purification of the multimer. If a C-terminal extension peptide is incorporated, it desirably incorporates a Pro residue as its initial residue, so that treatment of the resulting multimer with acid cleaves not only the C-terminal extension but also at the C-terminus of each GLP-2 peptide unit within the multimer.

In a most preferred embodiment of the invention, there is provided a GLP-2 peptide multimer having the sequence illustrated in FIG. 4, comprising 6 units of [Gly$^2$]hGLP-2 and incorporating, as a linker, the sequence ProValSerGlyProArg (SEQ ID NO: 12).

The production of such a multimer can be achieved in any cellular host for which expression systems have been developed. GLP-2 and its analogs do not require post-translational modification for activity, and can thus be produced in a variety of bacterial as well as eukaryotic hosts.

In one embodiment, the multimer is expressed in bacterial cells, such as *E. coli* cells, using expression systems adapted and well established for this purpose. A polynucleotide encoding the multimer can for instance be incorporated for expression within cassettes that drive expression from such promoters as lac, tac, trp, T7 and the like. The strain of *E. coli* chosen as host can also vary widely, and includes DH5, JM101 and BL21 among others. Vectors useful in transforming the selected host will typically include plasmids that incorporate origins of replication and selectable markers that enable detection and selective survival of the transformants.

Similarly, a variety of eukaryotic hosts and expression systems can be exploited. These include *Saccharomyces cerevisiae* and expression systems based on the mating factor alpha system, *Aspergillus nidulans* hosts utilizing the alcohol dehydrogenase (alcA) system, or *Aspergillus nidulans* utilizing the glucoamylase gene-based expression system, as well as mammalian cell systems such as the COS cell systems and the CHO-based systems.

Polynucleotides encoding the GLP-2 multimer can of course be produced synthetically de novo, or can be prepared from DNA coding for the GLP-2 peptide unit following a series of amplification and ligation steps, all in accordance with standard practise, and as exemplified herein.

The culturing conditions chosen for the transformed cellular host will also depend of course on the host species, and on the expression system utilized. In one embodiment, where the host is an *E. coli* species and the expression system relies on the tac promoter, the transformant will be cultured at commercial scale in the presence of antibiotic to maintain selective pressure on transformants. At or near log growth phase, the culture will receive IPTG to de-repress the promoter and allow expression to commence. Culturing can be performed at commercial scale of at or beyond about 200 litres.

Following culturing, the expressed GLP-2 multimer can be isolated by size selection chromatography, by ion-exchange chromatography, or by affinity chromatography particularly in the case where an affinity tag is incorporated in the multimer. When the multimer is produced as an intracellular product, the cultured cells can be treated in a first step to lyse the cells and release the multimer and other intracellular products, for instance using 8M urea or 6M guanidine hydrochloride or mechanical cell disruptions such as a homogenizer or sonicator. It is not necessary to separate the contents for further processing. In an embodiment of the invention, the products of lysis are treated in situ to establish dissociating conditions, such as by the addition of guanidinium chloride, and the mixture is then pH adjusted with HCl, or equivalent acid, to introduce acid conditions, in the pH range from about 1-3. At this pH, the Asp-Pro site is disrupted at each interface between the C-terminus of a GLP-2 peptide unit and the N-terminus of the linker. The resulting cleavage products, including GLP-2 peptide units bearing linker residues at the N-terminus, can then be isolated by any convenient means such as by HPLC, by size exclusion chromatography, by ion-exchange chromatography, or by affinity chromatography. The recovered products can then be subjected to an enzyme cleavage step in which exposure to thrombin results in the removal of residual linker at the N-terminus of each GLP-2 unit. The result is a multi-molar yield of GLP-2 peptides from a single GLP-2 multimer, each GLP-2 peptide having N- and C-termini that, as desired, are authentic and lacking in any undesired chemical modification.

As noted in the examples that follow, production by this method has produced [Gly2]hGLP-2 as a terminally authentic product having a mass (3752.59) that is essentially equivalent to theoretical (3751.99).

The GLP-2 peptide so produced is formulated, on an aspect of the present invention, for pharmaceutical use by forming a pharmaceutical composition in which a therapeutically useful amount of the peptide is combined with a pharmaceutically acceptable carrier. In one embodiment, the composition is formulated for parenteral administration, and comprises a unit dose of the GLP-2 peptide and an aqueous vehicle that is buffered to within a physiologically tolerable pH range and tonicity, e.g., pH 4-8, using for instance phosphate buffer saline as the vehicle. The formulation can also comprise a stabilizing agent, such as histidine, as disclosed in WO 01/49314, or a depot agent such as gelatin as disclosed in U.S. Pat. No. 5,789,379, the disclosures of which are incorporated herein by reference. Unit doses of the GLP-2 peptide lie typically within the range from 0.1 to 50 mg in an injection volume of about 1 mL.

The following examples are given to illustrate the present invention. It should be understood, however, that the invention is not to be limited to the specific conditions or details described in these examples. Throughout the specification, any and all references to a publicly available document, including a U.S. patent, are specifically incorporated by reference.

EXAMPLES

Various multimer constructs of $[Gly^2]$hGLP-2 gene can be made in a one pot reaction by taking advantage of the restriction endonuclease, BsaI. This endonuclease recognizes the non-palindromic sequence (GGTCTC), so that the linker and $[Gly^2]$hGLP-2 genes can be ligated in only one direction, head to tail ligation.

To obtain the maximum level of expression, the multimer gene constructs were inserted into a plasmid under the control of bacteriophage T7 promoter. Using this strategy, seven multimer constructs were obtained, containing 2 to 7 $[Gly^2]$ hGLP-2 gene units (from dimer to heptamer). The multimer genes were expressed after induction by IPTG. The greatest level of expression was found from hexamer and heptamer constructs.

A convenient cell lysis and acid cleavage method was also developed. After induction, the cell pellet was lysed with 6M guanidine hydrochloride and centrifuged. The supernatant solution was pH-adjusted to 1.8 by addition of HCl. Thus, cell lysis and acid cleavage were accomplished in very simple steps without any purification between lysis and acid cleavage. It may be possible to achieve cell lysis and acid cleavage in a single reaction, if 6M guanidine hydrochloride is pH adjusted to 1.8 with HCl and then it is added to *E. coli* cell pellet.

The acid cleaved products were purified by HPLC using a C18 column and then treated with thrombin to obtain mature $[Gly^2]$hGLP-2, which was further purified by HPLC using the same $C_{18}$ column. Only two HPLC steps (first after acid cleavage and second after thrombin cleavage) were needed to purify $[Gly^2]$hGLP-2, and the purified [Gly2]hGLP-2 was confirmed to be authentic $[Gly^2]$hGLP-2 by mass spectrometry.

Example 1

Gene Construction

To construct multimers of $[Gly^2]$hGLP-2 gene, a $[Gly^2]$ hGLP-2 gene, as shown below, was first amplified by PCR using a plasmid, pG3M, which carried a codon optimized $[Gly^2]$hGLP-2 gene and was re-named as pEW3G.

As shown in FIG. 1, the forward PCR primer sequence (Primer KS1-5) contained NdeI and BsaI endonuclease recognition sites, and thrombin cleavage site, which are followed by 18 nucleotides encoding the first six amino acids of [Gly$^2$] hGLP-2.

The reverse PCR primer (Primer KS2-3) contained BamHI and BsaI endonuclease recognition sites, acid cleavage site, and an 18 nucleotide sequence, which encode the last six amino acid residues of [Gly$^2$]hGLP-2.

For PCR reaction, the lower PCR reaction mixture was first prepared in a PCR tube. The lower mixture contained 41 µL of water, 5 µL of 10× TsgPlus buffer, 2 µL of deoxynucleotide mixture (2.5 mM each), 1 µL of primer KS1-5 (100 µM), and 1 µL of primer KS2-3 (100 µM). To the lower mixture, a piece of Ampliwax® was added and heated at 65° C. for 5 min and then cooled to room temperature on a bench. After a thin layer of wax was formed, the upper mixture contained 43.5 µL of water, 5 µL of 10× TsgPlus buffer, 0.2 ng of plasmid, pG3M, in 1 µL, and 0.5 µL of Tsg Plus enzyme. Tsg Plus enzyme was a mixture of Tsg DNA polymerase and Pfu DNA polymerase. The 10× Tsg Plus buffer contained 200 mM Tris-HCl (pH8.8), 100 mM KCl, 100 mM (NH$_4$)$_2$SO$_4$, 20 mM MgSO$_4$, 1% Triton X-100, and 1 mg/mL bovine serum albumin.

The thermocycler conditions were as follows:
Step 1: 95° C. for 2 min
Step 2: 95° C. for 1 min
Step 3: 50° C. for 1 min
Step 4: 72° C. for 15 sec
Step 5: Go to Step 2 and repeat Step 2 through Step 4 nine more times
Step 6: 95° C. for 1 min
Step 7: 65° C. for 30 sec
Step 8: 72° C. for 15 sec
Step 9: Go to Step 6 and repeat Step 6 through Step 8 nineteen more times
Step 10: 72° C. for 5 min
Step 11: 4° C. overnight After the whole cycle of PCR reaction, as described above, the expected product (a DNA band of approximately 140 bp), and as shown in FIG. 2, was confirmed by 1.5% agarose gel electrophoresis.

Forty µL out of the 100 µL PCR reaction mixture were purified using a QIA ExII kit according to the manufacturer's instruction, and then digested with BamHI and NdeI restriction enzymes. The digested DNA was separated by 2% agarose gel electrophoresis, the DNA band was cut out of the gel and then purified using QIA ExII. The purified PCR product digested with the two enzymes and purified was ligated into pET29a, which was previously digested with the same two restriction enzymes, NdeI and BamHI. The ligation was performed using Quick T4 DNA ligase at room temperature for 6 minutes.

Next, competent cells of E. coli DH5α were transformed with the ligation product. To 50 µL of thawed competent cells in a microfuge tube (1.8 mL capacity), 3 µL out of 21 µL ligation mixture were added. The competent cell mixture was kept on ice for 30 min, heat-shocked at 37° C. for 20 sec, and then kept on ice for 2 minutes. To the heat-shocked cells, 900 µL of pre-warmed Super Optimal Catabolite ("SOC") medium (37° C.) was added. After shaking the cell suspension at 225 rpm at 37° C. for 1 hour, 50 µL and 200 µL of the cell suspension were spread on LB agar plates containing kanamycin (50 µg/mL) and incubated at 37° C. overnight.

Single colonies were isolated from the agar plates the next day, and cultured in 7 mL of LB broth containing kanamycin (50 µg/mL) at 37° C. at 250 rpm overnight. Six mL out of 7 mL culture were centrifuged at 3,000 rpm for 15 min and plasmid was isolated from the cell pellet using QIAprep Spin Plasmid Miniprep kit.

To identify if the plasmid carried the insert, the isolated plasmid was digested by a restriction enzyme, PmlI, at 37° C. for 2 hours and then separated by 0.8% agarose gel electrophoresis. The plasmid was also digested by BsaI enzyme at 50° C. for 2.5 hours and analyzed on 1.5% agarose gel. As seen in FIG. 2, the PCR amplified insert carried a single PmlI site and two BsaI sites, but the vector, pET29a, did not carry those restriction enzyme sites. Therefore, only the plasmid, which carried the insert, was digested by PmlI and BsaI.

The insert portion of the plasmid was then sequenced from both directions using the two primers shown below (Forward and Reverse primers) to confirm the correct sequence of the insert on the plasmid. One of the plasmids, which carried the single insert with a correct nucleotide sequence, was designated as pKS35.

Example 2

Vector Construction

To construct multimers of [Gly$^2$]hGLP-2 gene, pKS35 was digested with BsaI at 50° C. for 2.5 hour and separated on 1.5% agarose gel. The larger DNA band (the vector portion) was cut out of the gel and DNA was extracted from the gel piece using QIA quick gel extraction kit. The smaller DNA band (the insert, approximately 110 bp) was cut out of the gel and the DNA was extracted using QIA ExII. The large vector portion was further treated with calf intestine alkaline phosphatase (CIP) to minimize self-ligation of the vector and purified by QIAPCR purification kit.

The CIP-treated vector DNA and the smaller insert DNA were mixed and ligated using Quick T4 ligase. The ligation mixture was used to transform DH5α, as described above, and then the bacteria cells were plated 2× Yeast Extract (2× YE) agar plates containing kanamycin (30 µg/mL).

To examine the number of [Gly$^2$]hGLP-2 gene units present on plasmid in each transformant, the inserts were directly amplified from heat-lysed E. coli cells by PCR and examined by agarose gel electrophoresis. As shown below, the forward primer used for the PCR (KS003-5) was a 20 base oligo nucleotide, which annealed to the phage T7 promoter region on pET29a. The reverse primer (KS004-3) was a 19 base oligonucleotide, which bound to the T7 transcription terminator region on the plasmid.

```
Forward Primer:    TAATACGACTCACTATAGGG
                   (SEQ ID NO: 13)

Reverse Primer:    GCTAGTTATTGCTCAGCGG
                   (SEQ ID NO: 14)
```

The PCR lower mixture contained 42 µL of water, 5 µL of 10× Tsg Plus buffer, 2 µL of deoxynucleotide mixture (2.5 mM each), 0.5 µL of 100 µM forward primer KS003-5, and 0.5 µL of 100 µM reverse primer KS004-3 in the total of 50 µL. A piece of Ampliwax was added to the lower mixture in a PCR tube, heated at 63° C. for 5 minutes, and then solidified at room temperature. To the top of solidified wax, the upper mixture (50 µL) was added. The upper mixture contained 44.5 µL of water, 5 µL of 10× Tsg Plus buffer, and 0.5 µL of Tsg Plus enzyme. Next, a single colony among many transformants was picked with a sterile toothpick from agar plate and suspended in the upper mixture. The PCR tube was then subjected to the PCR heating cycles using a thermocycler, as described below.

The thermocycler conditions were as follows:
Step 1: 95° C. for 5 min
Step 2: 95° C. for 1 min
Step 3: 55° C. for 30 sec
Step 4: 72° C. for 1 min
Step 5: Go to Step 2 and repeat Step 2 through Step 4 twenty nine more times
Step 6: 72° C. for 10 min
Step 7: 4° C. overnight The PCR products were separated by 1.5% agarose gel electrophoresis and seven different sizes of PCR products were detected on the gel. By comparison with DNA size markers (100 bp ladder), they were identified as monomer, dimer, trimer, tetramer, pentamer, hexamer and heptamer. These multimers were also subjected to nucleotide sequencing analysis, which demonstrated that all had correct sequences of multimers.

Example 3

Transformation and Culturing

The [Gly$^2$]hGLP-2 multimer constructs were cloned into a plasmid pET29a in such a way that they were expressed under the control of phage T7 promoter. E. coli RNA polymerase cannot recognize the T7 promoter. T7 RNA polymerase is required for the transcription from T7 promoter. E. coli strain, BLR(DE3), carries a phage T7 RNA polymerase gene on its chromosome. Moreover, recA gene in BLR(DE3) is inactivated so that the chance of losing [Gly$^2$]hGLP-2 gene units in the multimer constructs by homologous recombination is minimal in this strain. Both DH5α and BLR(DE3) strains are available commercially, as is the T7 system used herein.

The pET29a carrying a hexamer construct of [Gly$^2$] hGLP-2 was designated as pKS58 and isolated from the transformant cells using Qiagen Plasmid Midi Prep kit. The frozen competent cells of BLR(DE3) (20 μL) were thawed, mixed with 1 μL of pKS58, kept on ice for 5 minutes, heat-shocked at 42° C. for 30 sec, and then kept on ice for 2 minutes. To the cell mixture, 80 μL of SOC medium was added and incubated at 37° C. at 250 rpm for 1 hour. Portions of cell suspension (20 and 50 μL) were plated on 2× YE agar plates containing kanamycin (30 μg/mL) and incubated at 37° C. overnight.

For expression, a single colony from each of the transformation plates of BLR(DE3), carrying a [Gly$^2$]hGLP-2 gene multimer unit, was suspended in 50 mL of 2× YE broth containing kanamycin (30 μg/mL) in a 250 mL Erlenmeyer flask and shaken at 37° C. at 300 rpm overnight. An aliquot (200 μL) of the culture was added into 50 mL of pre-warmed 2×YE broth containing kanamycin (30 μg/mL) and shaken at 37° C. at 300 rpm. After 2 hours and 10 minutes when O.D. at 600 nm was approximately 0.35, IPTG was added to make a final concentration of 2 mM to induce the multimer gene.

At 2 and 3 hours after addition of IPTG, 2 mL of cell suspension were harvested and microfuged at 15,000 rpm for 15 minutes. The cell pellets were lysed with 50 μL of cell lysis buffer at 100° C. for 5 minutes. A portion of the cell lysate (12 μL) was mixed with 3 μL of SDS-PAGE loading buffer and proteins were separated by SDS-PAGE. The proteins on the gels were stained with Coomassie Blue. The expression of multimer constructs was examined by comparison with the protein molecular weight markers and the protein profile of uninduced cells.

Example 4

Multimer Processing and Peptide Isolation

After induction, the cells were harvested by centrifugation and one gram of the fresh cell pellets were lysed in 20 mL of 6M guanidine hydrochloride. The cell suspension was incubated on ice for 1 hour with occasional mixing and centrifuged at 12,000×g for 30 min. After addition of 30 mL of 6M guanidine hydrochloride to the supernatant solution, the pH of supernatant solution was adjusted to 1.8 by adding drops of 1N-HCl first and 0.1N-HCl and then incubated at 65° C. for 12-14 hours with gentle swirling. The reaction mixture was then separated by HPLC using a $C_{18}$ column and the elution by an acetonitrile gradient from 30 to 60% in 0.1% trifluoroacetic acid.

The acid-cleaved product peak ([Gly$^2$]hGLP-2 with a short peptide linker) was collected and dried. Next, the dried material was dissolved in thrombin buffer (20 mM Tris, 150 mM NaCl, 2.5 mM CaCl$_2$, pH8.4) and treated with thrombin at 37° C. overnight and the reaction was then stopped by addition of ACN 20% to final volume. The digestion product was then purified by HPLC using the same conditions described above.

The digestion product was then subjected to analysis by mass spectrometry, using a Micromass Quattro Micro™ mass spectrometer equipped with a Z-spray source operating in the positive ion mode with the following parameters: Data range: m/z 400-1600; Cone Voltage: 30-35 V; Source Temperature: 80° C.; Desolvation Temperature: 200° C.; Flow injection was via an HP1100; Solvent: 50:50 Acetonitrile:Water+0.1% formic acid; Software: Data were acquired using MassLynx 4.0. Calibration was performed using an MS spectrum of myoglobin and histatin 5.

As noted in FIG. 5, the mass of the predominant peak, representing authentic, recombinant (genetically produced) [Gly$^2$]hGLP-2 has a mass that is 3752.59, which is essentially the same as the theoretical mass of 3751.99.

The recovery of GLP-2 monomer from the multimer can also conveniently be achieved in a "one-pot" reaction using the multimer as reagent and providing the authentic, mature monomer as end-product, without requiring numerous separation of intermediate products and transfer steps.

With reference to the example provided above, the one pot process eliminates the step of cell lysis by 6M guanidine HCl, and first mechanically disrupts the expression host cells using for instance a homogenizer, or a sonicator. After cell disruption, the pH of the suspension is brought down, for instance to pH 1-3, by addition for instance of HCl. As described above, the suspension is then incubated at an appropriate temperature, such as 40-80C e.g., 65C, to complete the acid cleavage of multimer to produce the monomer intermediates bearing the N-terminal peptide linkers. The pH of the reaction mixture is then elevated, for instance using Tris-HCl, to within the pH range suitable for thrombin activity e.g., 7.5-9.0 and preferably about 8.4. The thrombin is then added to cause cleavage of the N-terminal peptide linkers, thereby to generate the mature GLP-2 product bearing authentic termini.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

We claim:

1. A process for preparing a GLP-2 peptide, comprising: providing a single-chain protein multimer comprising at least two units of a GLP-2 peptide coupled tandemly by a linker consisting of the amino acid sequence ProValSerGlyProArg (SEQ ID NO: 12), wherein the single-chain protein multimer comprises an acid cleavage site between the Asp residue at the C-terminus of each internal GLP-2 unit and the N-terminal Pro of the linker, wherein the linker comprises a thrombin enzyme recognition sequence consisting of the amino acid sequence ValSerGlyProArg (SEQ ID NO: 11) abutting the N-terminus of each internal GLP-2 unit, wherein the single-chain protein multimer comprises a thrombin enzyme cleavage site between the Arg residue at the C-terminus of the linker and the first residue of the GLP-2 peptide at the N-terminus of each internal GLP-2 unit;

cleaving the peptide bond at the acid cleavage site under conditions, wherein the pH is adjusted to a pH from about 1 to about 3 cleaving the peptide bond at the thrombin enzyme cleavage site with a thrombin enzyme;

thereby liberating said at least two GLP-2 peptide units, wherein each GLP-2 peptide unit has an authentic N- and C-terminal residue; and isolating the resulting GLP-2 peptide units.

2. The process according to claim 1, comprising:
a) first cleaving the peptide bond at the acid cleavage site with acid,
b) isolating the resulting cleaved multimer;
c) cleaving the peptide bond at the thrombin enzyme cleavage site with thrombin enzyme, and
d) isolating the resulting GLP-2 peptide units having authentic termini.

3. The process according to claim 1, wherein the step of cleaving the peptide bond at the acid cleavage site acid is performed at the time of extracting the GLP-2 peptide multimer from a cellular host producing said multimer.

4. The process according to claim 1, wherein the steps of cleaving the peptide bond at the acid cleavage site and cleaving the peptide bond at the thrombin cleavage site are performed without separation of reaction products prior to cleaving the peptide bond at the thrombin enzyme cleavage site with thrombin enzyme.

* * * * *

SEQUENCE LISTING

<160> NUMBER OF SEQ ID NOS: 14

<210> SEQ ID NO 1
<211> LENGTH: 6004
<212> TYPE: DNA
<213> ORGANISM: Artificial Sequence
<220> FEATURE:
<223> OTHER INFORMATION: Description of Artificial Sequence: Synthetic construct
<220> FEATURE:
<221> NAME/KEY: CDS
<222> LOCATION: (5076)..(5795)

<400> SEQUENCE: 1

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct tgacgttgg agtccacgtt      300 ctttaatagt ggactcttgt tccaaactgg aacaacactc aaccctatct cggtctattc     360
ttttgattta aagggatttt gccgatttc ggcctattgg ttaaaaaatg agctgattta      420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga gacgaaatac gcgatcgctg ttaaaaggac     960
aattacaaac aggaatcgaa tgcaaccggc gcaggaacac tgccagcgca tcaacaatat    1020
tttcacctga atcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa    1440 cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actctttttc cgaaggtaac tggcttcagc    1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata gtcgtgtct taccgggttg gactcaagac gatagttacc ggataaggcg     1800
cagcggtcgg gctgaacggg gggttcgtgc acacagccca gcttggagcg aacgacctac    1860
```

```
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccagggggaa acgcctggta tctttatagt cctgtcgggt ttcgccacct ctgacttgag    2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacgcggga tataacatga gctgtcttcg gtatcgtcgt    3780
atcccactac cgagatgtcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
```

-continued

```
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa agacaccgg     4560 catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatcga tctcgatccc    4980
gcgaaattaa tacgactcac tatagggaa ttgtgagcgg ataacaattc cctctagaa     5040 ataattttgt ttaactttaa gaaggagata tacat atg gtc tca ggt ccg cgt     5093
                                        Met Val Ser Gly Pro Arg
                                         1               5 cat ggt gac ggt tct ttc tct gac gaa atg aac acc atc ctg gac aac    5141
His Gly Asp Gly Ser Phe Ser Asp Glu Met Asn Thr Ile Leu Asp Asn
            10                  15                  20 ctg gct gca cgt gac ttc atc aac tgg ctg atc cag acc aaa atc acc    5189
Leu Ala Ala Arg Asp Phe Ile Asn Trp Leu Ile Gln Thr Lys Ile Thr
        25                  30                  35 gac ccg gtc tca ggt ccg cgt cat ggt gac ggt tct ttc tct gac gaa    5237
Asp Pro Val Ser Gly Pro Arg His Gly Asp Gly Ser Phe Ser Asp Glu
    40                  45                  50 atg aac acc atc ctg gac aac ctg gct gca cgt gac ttc atc aac tgg    5285
Met Asn Thr Ile Leu Asp Asn Leu Ala Ala Arg Asp Phe Ile Asn Trp
55                  60                  65                  70 ctg atc cag acc aaa atc acc gac ccg gtc tca ggt ccg cgt cat ggt    5333
Leu Ile Gln Thr Lys Ile Thr Asp Pro Val Ser Gly Pro Arg His Gly
                75                  80                  85 gac ggt tct ttc tct gac gaa atg aac acc atc ctg gac aac ctg gct    5381
Asp Gly Ser Phe Ser Asp Glu Met Asn Thr Ile Leu Asp Asn Leu Ala
            90                  95                 100 gca cgt gac ttc atc aac tgg ctg atc cag acc aaa atc acc gac ccg    5429
Ala Arg Asp Phe Ile Asn Trp Leu Ile Gln Thr Lys Ile Thr Asp Pro
        105                 110                 115 gtc tca ggt ccg cgt cat ggt gac ggt tct ttc tct gac gaa atg aac    5477
Val Ser Gly Pro Arg His Gly Asp Gly Ser Phe Ser Asp Glu Met Asn
    120                 125                 130 acc atc ctg gac aac ctg gct gca cgt gac ttc atc aac tgg ctg atc    5525
Thr Ile Leu Asp Asn Leu Ala Ala Arg Asp Phe Ile Asn Trp Leu Ile
135                 140                 145                 150 cag acc aaa atc acc gac ccg gtc tca ggt ccg cgt cat ggt gac ggt    5573
Gln Thr Lys Ile Thr Asp Pro Val Ser Gly Pro Arg His Gly Asp Gly
                155                 160                 165 tct ttc tct gac gaa atg aac acc atc ctg gac aac ctg gct gca cgt    5621
Ser Phe Ser Asp Glu Met Asn Thr Ile Leu Asp Asn Leu Ala Ala Arg
            170                 175                 180 gac ttc atc aac tgg ctg atc cag acc aaa atc acc gac ccg gtc tca    5669
Asp Phe Ile Asn Trp Leu Ile Gln Thr Lys Ile Thr Asp Pro Val Ser
        185                 190                 195
```

```
ggt ccg cgt cat ggt gac ggt tct ttc tct gac gaa atg aac acc atc       5717
Gly Pro Arg His Gly Asp Gly Ser Phe Ser Asp Glu Met Asn Thr Ile
        200                 205                 210 ctg gac aac ctg gct gca cgt gac ttc atc aac tgg ctg atc cag acc       5765
Leu Asp Asn Leu Ala Ala Arg Asp Phe Ile Asn Trp Leu Ile Gln Thr
215                 220                 225                 230 aaa atc acc gac ccg gtc tca ggt ccg cgc taatgaggat ccgaattcga         5815
Lys Ile Thr Asp Pro Val Ser Gly Pro Arg
                235                 240 gctccgtcga caagcttgcg gccgcactcg agcaccacca ccaccaccac tgagatccgg     5875
ctgctaacaa agcccgaaag gaagctgagt tggctgctgc caccgctgag caataactag    5935
cataacccct tggggcctct aaacgggtct tgaggggttt tttgctgaaa ggaggaacta    5995
tatccggat                                                             6004

<210> SEQ ID NO 2
<211> LENGTH: 240
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 2

Met Val Ser Gly Pro Arg His Gly Asp Gly Ser Phe Ser Asp Glu Met
  1               5                  10                  15

Asn Thr Ile Leu Asp Asn Leu Ala Ala Arg Asp Phe Ile Asn Trp Leu
             20                  25                  30

Ile Gln Thr Lys Ile Thr Asp Pro Val Ser Gly Pro Arg His Gly Asp
         35                  40                  45

Gly Ser Phe Ser Asp Glu Met Asn Thr Ile Leu Asp Asn Leu Ala Ala
     50                  55                  60

Arg Asp Phe Ile Asn Trp Leu Ile Gln Thr Lys Ile Thr Asp Pro Val
 65                  70                  75                  80

Ser Gly Pro Arg His Gly Asp Gly Ser Phe Ser Asp Glu Met Asn Thr
                 85                  90                  95

Ile Leu Asp Asn Leu Ala Ala Arg Asp Phe Ile Asn Trp Leu Ile Gln
            100                 105                 110

Thr Lys Ile Thr Asp Pro Val Ser Gly Pro Arg His Gly Asp Gly Ser
        115                 120                 125

Phe Ser Asp Glu Met Asn Thr Ile Leu Asp Asn Leu Ala Ala Arg Asp
    130                 135                 140

Phe Ile Asn Trp Leu Ile Gln Thr Lys Ile Thr Asp Pro Val Ser Gly
145                 150                 155                 160

Pro Arg His Gly Asp Gly Ser Phe Ser Asp Glu Met Asn Thr Ile Leu
                165                 170                 175

Asp Asn Leu Ala Ala Arg Asp Phe Ile Asn Trp Leu Ile Gln Thr Lys
            180                 185                 190

Ile Thr Asp Pro Val Ser Gly Pro Arg His Gly Asp Gly Ser Phe Ser
        195                 200                 205

Asp Glu Met Asn Thr Ile Leu Asp Asn Leu Ala Ala Arg Asp Phe Ile
    210                 215                 220

Asn Trp Leu Ile Gln Thr Lys Ile Thr Asp Pro Val Ser Gly Pro Arg
225                 230                 235                 240

<210> SEQ ID NO 3
```

<211> LENGTH: 160
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (11)..(145)

<400> SEQUENCE: 3

```
ggaattccat atg gtc tca ggt ccg cgt cat ggt gac ggt tct ttc tct        49
           Met Val Ser Gly Pro Arg His Gly Asp Gly Ser Phe Ser
            1               5                  10 gac gaa atg aac acc atc ctg gac aac ctg gct gca cgt gac ttc atc        97
Asp Glu Met Asn Thr Ile Leu Asp Asn Leu Ala Ala Arg Asp Phe Ile
         15                  20                  25 aac tgg ctg atc cag acc aaa atc acc gac ccg gtc tca ggt ccg cgc       145
Asn Trp Leu Ile Gln Thr Lys Ile Thr Asp Pro Val Ser Gly Pro Arg
 30                  35                  40                  45 taatgaggat ccgcg                                                       160
```

<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 4

```
Met Val Ser Gly Pro Arg His Gly Asp Gly Ser Phe Ser Asp Glu Met
 1               5                  10                  15

Asn Thr Ile Leu Asp Asn Leu Ala Ala Arg Asp Phe Ile Asn Trp Leu
             20                  25                  30

Ile Gln Thr Lys Ile Thr Asp Pro Val Ser Gly Pro Arg
         35                  40                  45
```

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (11)..(46)

<400> SEQUENCE: 5

```
ggaattccat atg gtc tca ggt ccg cgt cat ggt gac ggt tct ttc               46
           Met Val Ser Gly Pro Arg His Gly Asp Gly Ser Phe
            1               5                  10
```

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 6

```
Met Val Ser Gly Pro Arg His Gly Asp Gly Ser Phe
 1               5                  10
```

```
<210> SEQ ID NO 7
<211> LENGTH: 51
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7
cgcggatcct cattagcgcg gaccagagac cgggtcggtg attttggtct g              51

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

Arg Pro Gly Ser Val Pro Asp Thr Ile Lys Thr Gln
  1               5                  10

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asp Asp Asp Asp Lys
  1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Glu Gly Arg
  1

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Ser Gly Pro Arg
  1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

```
Pro Val Ser Gly Pro Arg
  1               5

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
taatacgact cactataggg                                              20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gctagttatt gctcagcgg                                               19
```